United States Patent
Slee et al.

(10) Patent No.: US 10,456,151 B2
(45) Date of Patent: Oct. 29, 2019

(54) METHODS AND APPARATUS FOR FLOW RESTORATION

(71) Applicant: Covidien LP, Mansfield, MA (US)

(72) Inventors: Earl Howard Slee, Laguna Niguel, CA (US); Thomas Wilder, Newport Beach, CA (US); Thomas McCarthy, San Clemente, CA (US); Mark Philip Ashby, Laguna Niguel, CA (US); Sanjay Shrivastava, Irvine, CA (US)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 14/885,826

(22) Filed: Oct. 16, 2015

(65) Prior Publication Data

US 2016/0100849 A1    Apr. 14, 2016

Related U.S. Application Data

(63) Continuation of application No. 14/136,252, filed on Dec. 20, 2013, now Pat. No. 9,161,766, which is a
(Continued)

(51) Int. Cl.
*A61B 17/221*    (2006.01)
*A61F 2/90*    (2013.01)
(Continued)

(52) U.S. Cl.
CPC ............ *A61B 17/221* (2013.01); *A61B 17/22* (2013.01); *A61F 2/90* (2013.01);
(Continued)

(58) Field of Classification Search
CPC .................. A61B 17/221; A61B 17/22; A61B 2017/22094; A61B 2017/22034;
(Continued)

(56) References Cited

U.S. PATENT DOCUMENTS 2,709,999 A    6/1955    Nagel
3,174,851 A    3/1965    Buehler et al.
(Continued)

FOREIGN PATENT DOCUMENTS

BR    9604566 A    9/1998
CA    2389374 A1    5/2001
(Continued)

OTHER PUBLICATIONS

US 6,056,761 A, 05/2000, Gia (withdrawn)
(Continued)

*Primary Examiner* — Thomas M McEvoy
(74) *Attorney, Agent, or Firm* — Fortem IP LLP; Matthew Lincicum

(57) ABSTRACT

Methods for restoring blood flow in occluded blood vessels using an apparatus having a self-expandable distal segment that is pre-formed to assume a superimposed structure in an unconstrained condition but can be made to take on a volume-reduced form making it possible to introduce it with a microcatheter and a push wire arranged at the proximal end, with the distal segment in its superimposed structure assuming the form of a longitudinally open tube and having a mesh structure of interconnected strings or filaments or struts. In a preferred embodiment, the distal segment has a tapering structure at its proximal end where the strings or filaments or struts converge at a connection point.

34 Claims, 10 Drawing Sheets

Related U.S. Application Data continuation of application No. 13/678,464, filed on Nov. 15, 2012, now Pat. No. 8,679,142, which is a continuation of application No. 12/918,795, filed as application No. PCT/US2009/034774 on Feb. 20, 2009, now Pat. No. 8,940,003.

(60) Provisional application No. 61/030,838, filed on Feb. 22, 2008.

(51) Int. Cl.
  *A61B 17/22* (2006.01)
  *A61F 2/91* (2013.01)
  *A61F 2/92* (2013.01)

(52) U.S. Cl.
  CPC ............... *A61B 2017/2215* (2013.01); *A61B 2017/22034* (2013.01); *A61B 2017/22094* (2013.01); *A61F 2/91* (2013.01); *A61F 2/92* (2013.01)

(58) Field of Classification Search
  CPC ...... A61B 2017/2215; A61F 2/90; A61F 2/91; A61F 2/92
  See application file for complete search history.

(56) References Cited

U.S. PATENT DOCUMENTS

| | | | |
|---|---|---|---|
| 3,351,463 | A | 11/1967 | Rozner |
| 3,506,171 | A | 4/1970 | Rupert |
| 3,753,700 | A | 8/1973 | Harrison et al. |
| 3,996,938 | A | 12/1976 | Clark, III |
| 4,046,150 | A | 9/1977 | Schwartz et al. |
| 4,299,255 | A | 11/1981 | Miller |
| 4,347,846 | A | 9/1982 | Dormia |
| 4,403,612 | A | 9/1983 | Fogarty |
| 4,611,594 | A | 9/1986 | Grayhack et al. |
| 4,612,931 | A | 9/1986 | Dormia |
| 4,650,466 | A | 3/1987 | Luther |
| 4,655,771 | A | 4/1987 | Wallsten |
| 4,733,665 | A | 3/1988 | Palmaz |
| 4,739,762 | A | 4/1988 | Palmaz |
| 4,793,348 | A | 12/1988 | Palmaz |
| 4,890,611 | A | 1/1990 | Monfort et al. |
| 4,993,481 | A | 2/1991 | Kamimoto |
| 4,998,539 | A | 3/1991 | Delsanti |
| 5,035,686 | A | 7/1991 | Crittenden |
| 5,057,114 | A | 10/1991 | Wittich |
| 5,071,407 | A | 12/1991 | Termin et al. |
| 5,100,423 | A | 3/1992 | Fearnot |
| 5,102,417 | A | 4/1992 | Palmaz |
| 5,190,058 | A | 3/1993 | Jones et al. |
| 5,192,286 | A | 3/1993 | Phan et al. |
| 5,195,984 | A | 3/1993 | Schatz |
| 5,197,978 | A | 3/1993 | Hess |
| 5,217,484 | A | 6/1993 | Marks |
| 5,222,964 | A | 6/1993 | Cooper |
| 5,222,971 | A | 6/1993 | Willard et al. |
| 5,275,622 | A | 1/1994 | Lazarus |
| 5,312,344 | A | 5/1994 | Grinfeld et al. |
| 5,327,885 | A | 7/1994 | Griffith |
| 5,330,482 | A | 7/1994 | Gibbs et al. |
| 5,344,395 | A | 9/1994 | Whalen |
| 5,354,295 | A | 10/1994 | Guglielmi et al. |
| 5,370,653 | A | 12/1994 | Cragg |
| 5,411,549 | A | 5/1995 | Peters |
| 5,423,829 | A | 6/1995 | Pham et al. |
| 5,425,739 | A | 6/1995 | Jessen |
| 5,449,372 | A | 9/1995 | Schmaltz et al. |
| 5,456,667 | A | 10/1995 | Ham et al. |
| 5,490,859 | A | 2/1996 | Mische et al. |
| 5,496,330 | A | 3/1996 | Bates et al. |
| 5,501,694 | A | 3/1996 | Ressemann et al. |
| 5,527,282 | A | 6/1996 | Segal |
| 5,527,326 | A | 6/1996 | Hermann et al. |
| 5,540,680 | A | 7/1996 | Guglielmi et al. |
| 5,540,707 | A | 7/1996 | Ressemann et al. |
| 5,569,245 | A | 10/1996 | Guglielmi et al. |
| 5,571,122 | A | 11/1996 | Kelly et al. |
| 5,573,520 | A | 11/1996 | Schwartz et al. |
| 5,624,449 | A | 4/1997 | Pham et al. |
| 5,643,309 | A | 7/1997 | Myler et al. |
| 5,649,906 | A | 7/1997 | Gory et al. |
| 5,653,743 | A | 8/1997 | Martin |
| 5,669,933 | A | 9/1997 | Simon et al. |
| 5,681,336 | A | 10/1997 | Clement et al. |
| 5,683,449 | A | 11/1997 | Marcade |
| 5,690,667 | A | 11/1997 | Gia |
| 5,695,469 | A | 12/1997 | Segal |
| 5,695,519 | A | 12/1997 | Summers et al. |
| 5,718,724 | A | 2/1998 | Goicoechea et al. |
| 5,720,764 | A | 2/1998 | Naderlinger |
| 5,743,905 | A | 4/1998 | Eder et al. |
| 5,749,883 | A | 5/1998 | Halpern |
| 5,759,192 | A | 6/1998 | Saunders |
| 5,769,882 | A | 6/1998 | Fogarty et al. |
| 5,792,145 | A | 8/1998 | Bates et al. |
| 5,792,157 | A | 8/1998 | Mische et al. |
| 5,795,322 | A | 8/1998 | Boudewijn |
| 5,800,454 | A | 9/1998 | Jacobsen et al. |
| 5,800,457 | A | 9/1998 | Gelbfih |
| 5,800,519 | A | 9/1998 | Sandock |
| 5,800,520 | A | 9/1998 | Fogarty et al. |
| 5,800,525 | A | 9/1998 | Bachinski et al. |
| 5,814,064 | A | 9/1998 | Daniel et al. |
| 5,824,037 | A | 10/1998 | Fogarty et al. |
| 5,827,304 | A | 10/1998 | Hart |
| 5,827,324 | A | 10/1998 | Cassell et al. |
| 5,836,868 | A | 11/1998 | Ressemann et al. |
| 5,848,964 | A | 12/1998 | Samuels |
| 5,851,206 | A | 12/1998 | Guglielmi et al. |
| 5,853,419 | A | 12/1998 | Imran |
| 5,855,578 | A | 1/1999 | Guglielmi et al. |
| 5,882,329 | A | 3/1999 | Patterson et al. |
| 5,891,128 | A | 4/1999 | Gia et al. |
| 5,895,385 | A | 4/1999 | Guglielmi et al. |
| 5,895,398 | A | 4/1999 | Wensel et al. |
| 5,897,567 | A | 4/1999 | Ressemann et al. |
| 5,904,698 | A | 5/1999 | Thomas et al. |
| 5,911,717 | A | 6/1999 | Jacobsen et al. |
| 5,911,734 | A | 6/1999 | Tsugita et al. |
| 5,913,895 | A | 6/1999 | Burpee et al. |
| 5,916,235 | A | 6/1999 | Guglielmi |
| 5,919,187 | A | 7/1999 | Guglielmi et al. |
| 5,922,019 | A | 7/1999 | Hankh et al. |
| 5,925,037 | A | 7/1999 | Guglielmi et al. |
| 5,925,061 | A | 7/1999 | Ogi et al. |
| 5,928,226 | A | 7/1999 | Guglielmi et al. |
| 5,928,260 | A | 7/1999 | Chin et al. |
| 5,935,139 | A | 8/1999 | Bates |
| 5,938,671 | A | 8/1999 | Katoh et al. |
| 5,938,697 | A | 8/1999 | Killion et al. |
| 5,941,869 | A | 8/1999 | Patterson et al. |
| 5,941,895 | A | 8/1999 | Myler et al. |
| 5,944,714 | A | 8/1999 | Guglielmi et al. |
| 5,947,962 | A | 9/1999 | Guglielmi et al. |
| 5,947,995 | A | 9/1999 | Samuels |
| 5,948,016 | A | 9/1999 | Jang |
| 5,951,599 | A | 9/1999 | McCrory |
| 5,954,743 | A | 9/1999 | Jang |
| 5,961,547 | A | 10/1999 | Razavi |
| 5,964,797 | A | 10/1999 | Ho |
| 5,968,013 | A | 10/1999 | Smith et al. |
| 5,972,016 | A | 10/1999 | Morales |
| 5,972,019 | A | 10/1999 | Engelson et al. |
| 5,972,219 | A | 10/1999 | Habets et al. |
| 5,976,120 | A | 11/1999 | Chow |
| 5,976,126 | A | 11/1999 | Guglielmi |
| 5,976,131 | A | 11/1999 | Guglielmi et al. |
| 5,980,514 | A | 11/1999 | Kupiecki et al. |
| 5,984,929 | A | 11/1999 | Bashiri et al. |
| 6,001,118 | A | 12/1999 | Daniel et al. |
| 6,010,449 | A | 1/2000 | Selmon et al. |

(56) References Cited

U.S. PATENT DOCUMENTS

| | | |
|---|---|---|
| 6,010,498 A | 1/2000 | Guglielmi |
| 6,010,521 A | 1/2000 | Lee et al. |
| 6,013,093 A | 1/2000 | Nott et al. |
| 6,015,424 A | 1/2000 | Rosenbluth et al. |
| 6,039,721 A | 3/2000 | Johnson |
| 6,051,020 A | 4/2000 | Goicoechea et al. |
| 6,059,814 A | 5/2000 | Ladd |
| 6,063,070 A | 5/2000 | Eder |
| 6,063,100 A | 5/2000 | Diaz et al. |
| 6,063,104 A | 5/2000 | Villar et al. |
| 6,063,111 A | 5/2000 | Hieshima et al. |
| 6,066,149 A | 5/2000 | Samson et al. |
| 6,066,158 A | 5/2000 | Engelson et al. |
| 6,077,260 A | 6/2000 | Wheelock et al. |
| 6,083,220 A | 7/2000 | Guglielmi et al. |
| 6,093,199 A | 7/2000 | Brown |
| 6,096,034 A | 8/2000 | Kupiecki et al. |
| 6,096,053 A | 8/2000 | Bates |
| 6,099,549 A | 8/2000 | Bosma et al. |
| 6,106,548 A | 8/2000 | Roubin et al. |
| 6,110,198 A | 8/2000 | Fogarty et al. |
| 6,117,167 A | 9/2000 | Goicoechea et al. |
| 6,118,001 A | 9/2000 | Owen et al. |
| 6,123,115 A | 9/2000 | Greenhalgh |
| 6,123,714 A | 9/2000 | Gia et al. |
| 6,129,755 A | 10/2000 | Mathis et al. |
| 6,136,006 A | 10/2000 | Johnson et al. |
| 6,146,396 A | 11/2000 | Konya et al. |
| 6,156,061 A | 12/2000 | Wallace et al. |
| 6,159,238 A | 12/2000 | Killion et al. |
| 6,159,239 A | 12/2000 | Greenhalgh |
| 6,164,339 A | 12/2000 | Greenhalgh |
| 6,165,178 A | 12/2000 | Bashiri et al. |
| 6,165,213 A | 12/2000 | Goicoechea et al. |
| 6,168,592 B1 | 1/2001 | Kupiecki et al. |
| 6,168,603 B1 | 1/2001 | Leslie et al. |
| 6,168,604 B1 | 1/2001 | Cano |
| 6,179,857 B1 | 1/2001 | Diaz et al. |
| 6,187,017 B1 | 2/2001 | Gregory, Jr. |
| 6,190,358 B1 | 2/2001 | Fitzmaurice et al. |
| 6,190,394 B1 | 2/2001 | Lind et al. |
| 6,192,944 B1 | 2/2001 | Greenhalgh |
| 6,193,708 B1 | 2/2001 | Ken et al. |
| 6,193,745 B1 | 2/2001 | Fogarty et al. |
| 6,203,552 B1 | 3/2001 | Bagley et al. |
| 6,210,364 B1 | 4/2001 | Anderson et al. |
| 6,214,025 B1 | 4/2001 | Thistle et al. |
| 6,217,609 B1 | 4/2001 | Haverkost |
| 6,221,096 B1 | 4/2001 | Aiba et al. |
| 6,231,598 B1 | 5/2001 | Berry et al. |
| 6,238,412 B1 | 5/2001 | Dubrul et al. |
| 6,238,430 B1 | 5/2001 | Klumb et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,686 B1 | 7/2001 | Rieu et al. |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,280,413 B1 | 8/2001 | Clark |
| 6,283,940 B1 | 9/2001 | Mulholland |
| 6,283,992 B1 | 9/2001 | Hankh et al. |
| 6,290,720 B1 | 9/2001 | Khosravi et al. |
| 6,302,906 B1 | 10/2001 | Goicoechea et al. |
| 6,305,436 B1 | 10/2001 | Andersen et al. |
| 6,306,141 B1 | 10/2001 | Jervis |
| 6,312,463 B1 | 11/2001 | Rourke et al. |
| 6,322,585 B1 | 11/2001 | Khosravi et al. |
| 6,325,815 B1 | 12/2001 | Kusleika et al. |
| 6,325,820 B1 | 12/2001 | Khosravi et al. |
| 6,325,822 B1 | 12/2001 | Chouinard et al. |
| 6,336,934 B1 | 1/2002 | Gilson et al. |
| 6,344,041 B1 | 2/2002 | Kupiecki et al. |
| 6,361,558 B1 | 3/2002 | Hieshima et al. |
| 6,371,969 B1 | 4/2002 | Tsugita et al. |
| 6,379,329 B1 | 4/2002 | Naglreiter et al. |
| 6,383,205 B1 | 5/2002 | Samson et al. |
| 6,390,993 B1 | 5/2002 | Cornish et al. |
| 6,402,771 B1 | 6/2002 | Palmer et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,443,971 B1 | 9/2002 | Boylan et al. |
| 6,443,972 B1 | 9/2002 | Bosma et al. |
| 6,454,775 B1 | 9/2002 | Demarais et al. |
| 6,454,780 B1 | 9/2002 | Wallace |
| 6,458,139 B1 | 10/2002 | Palmer et al. |
| 6,468,266 B1 | 10/2002 | Bashiri et al. |
| 6,468,301 B1 | 10/2002 | Amplatz et al. |
| 6,475,236 B1 | 11/2002 | Roubin et al. |
| 6,475,237 B2 | 11/2002 | Drasler et al. |
| 6,485,500 B1 | 11/2002 | Kokish et al. |
| 6,485,509 B2 | 11/2002 | Killion et al. |
| 6,485,524 B2 | 11/2002 | Strecker |
| 6,491,719 B1 | 12/2002 | Fogarty et al. |
| 6,500,182 B2 | 12/2002 | Foster |
| 6,514,273 B1 | 2/2003 | Voss et al. |
| 6,520,968 B2 | 2/2003 | Bates et al. |
| 6,530,935 B2 | 3/2003 | Wensel et al. |
| 6,533,811 B1 | 3/2003 | Ryan et al. |
| 6,537,294 B1 | 3/2003 | Boyle et al. |
| 6,551,341 B2 | 4/2003 | Boylan et al. |
| 6,551,342 B1 | 4/2003 | Shen et al. |
| 6,553,810 B2 | 4/2003 | Webb et al. |
| 6,554,842 B2 | 4/2003 | Heuser et al. |
| 6,554,849 B1 | 4/2003 | Jones et al. |
| 6,554,856 B1 | 4/2003 | Doorly et al. |
| 6,558,405 B1 | 5/2003 | McInnes |
| 6,562,066 B1 | 5/2003 | Martin |
| 6,569,179 B2 | 5/2003 | Teoh et al. |
| 6,569,193 B1 | 5/2003 | Cox et al. |
| 6,572,648 B1 | 6/2003 | Klumb et al. |
| 6,575,995 B1 | 6/2003 | Huter et al. |
| 6,575,997 B1 | 6/2003 | Palmer et al. |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,607 B1 | 7/2003 | Palmer et al. |
| 6,592,615 B1 | 7/2003 | Marcade et al. |
| 6,605,057 B2 | 8/2003 | Fitzmaurice et al. |
| 6,610,077 B1 | 8/2003 | Hancock et al. |
| 6,616,617 B1 | 9/2003 | Ferrera et al. |
| 6,620,152 B2 | 9/2003 | Guglielmi |
| 6,629,953 B1 | 10/2003 | Boyd |
| 6,632,241 B1 | 10/2003 | Hancock et al. |
| 6,635,081 B2 | 10/2003 | Khosravi et al. |
| 6,638,294 B1 | 10/2003 | Palmer |
| 6,641,590 B1 | 11/2003 | Palmer et al. |
| 6,645,224 B2 | 11/2003 | Gilson et al. |
| 6,652,505 B1 | 11/2003 | Tsugita |
| 6,652,548 B2 | 11/2003 | Evans et al. |
| 6,652,576 B1 | 11/2003 | Stalker |
| 6,656,214 B1 | 12/2003 | Fogarty et al. |
| 6,660,014 B2 | 12/2003 | Demarais et al. |
| 6,660,021 B1 | 12/2003 | Palmer et al. |
| 6,663,607 B2 | 12/2003 | Slaikeu et al. |
| 6,663,650 B2 | 12/2003 | Sepetka et al. |
| 6,666,829 B2 | 12/2003 | Cornish et al. |
| 6,669,723 B2 | 12/2003 | Killion et al. |
| 6,673,025 B1 | 1/2004 | Richardson et al. |
| 6,673,106 B2 | 1/2004 | Mitelberg et al. |
| 6,679,893 B1 | 1/2004 | Tran |
| 6,685,722 B1 | 2/2004 | Rosenbluth et al. |
| 6,685,738 B2 | 2/2004 | Chouinard et al. |
| 6,692,508 B2 | 2/2004 | Wensel et al. |
| 6,695,813 B1 | 2/2004 | Boyle et al. |
| 6,702,782 B2 | 3/2004 | Miller et al. |
| 6,702,843 B1 | 3/2004 | Brown et al. |
| 6,709,440 B2 | 3/2004 | Callol et al. |

(56) References Cited

U.S. PATENT DOCUMENTS

| | | |
|---|---|---|
| 6,716,178 B1 | 4/2004 | Kilpatrick et al. |
| 6,716,238 B2 | 4/2004 | Elliott |
| 6,723,108 B1 | 4/2004 | Jones et al. |
| 6,723,112 B2 | 4/2004 | Ho et al. |
| 6,730,104 B1 | 5/2004 | Sepetka et al. |
| 6,733,519 B2 | 5/2004 | Lashinski et al. |
| 6,743,236 B2 | 6/2004 | Barry et al. |
| 6,746,468 B1 | 6/2004 | Sepetka et al. |
| 6,764,506 B2 | 7/2004 | Roubin et al. |
| 6,773,454 B2 | 8/2004 | Wholey et al. |
| 6,790,237 B2 | 9/2004 | Stinson |
| 6,795,979 B2 | 9/2004 | Fournier |
| 6,802,851 B2 | 10/2004 | Jones et al. |
| 6,811,560 B2 | 11/2004 | Jones et al. |
| 6,818,013 B2 | 11/2004 | Mitelberg et al. |
| 6,818,015 B2 | 11/2004 | Hankh et al. |
| 6,821,291 B2 | 11/2004 | Bolea et al. |
| 6,824,558 B2 | 11/2004 | Parodi |
| 6,833,002 B2 | 12/2004 | Stack et al. |
| 6,833,003 B2 | 12/2004 | Jones et al. |
| 6,840,958 B2 | 1/2005 | Nunez et al. |
| 6,878,151 B2 | 4/2005 | Carrison et al. |
| 6,881,220 B2 | 4/2005 | Edwin et al. |
| 6,887,268 B2 | 5/2005 | Butaric et al. |
| 6,893,413 B2 | 5/2005 | Martin |
| 6,913,612 B2 | 7/2005 | Palmer et al. |
| 6,921,414 B2 | 7/2005 | Klumb et al. |
| 6,945,977 B2 | 9/2005 | Demarais et al. |
| 6,949,620 B2 | 9/2005 | Aida et al. |
| 6,953,468 B2 | 10/2005 | Jones et al. |
| 6,953,472 B2 | 10/2005 | Palmer et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 6,974,473 B2 | 12/2005 | Barclay et al. |
| 6,989,020 B2 | 1/2006 | Jones et al. |
| 6,991,641 B2 | 1/2006 | Diaz et al. |
| 6,994,723 B1 | 2/2006 | McMahon |
| 7,001,422 B2 | 2/2006 | Escamilla et al. |
| 7,004,954 B1 | 2/2006 | Voss et al. |
| 7,004,955 B1 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,037,331 B2 | 5/2006 | Mitelberg et al. |
| 7,041,116 B2 | 5/2006 | Goto et al. |
| 7,048,014 B2 | 5/2006 | Hyodoh et al. |
| 7,052,500 B2 | 5/2006 | Bashiri et al. |
| 7,056,328 B2 | 6/2006 | Arnott |
| 7,056,336 B2 | 6/2006 | Armstrong et al. |
| 7,058,456 B2 | 6/2006 | Pierce |
| 7,060,091 B2 | 6/2006 | Killion et al. |
| 7,089,218 B1 | 8/2006 | Visel |
| 7,097,653 B2 | 8/2006 | Freudenthal et al. |
| 7,101,380 B2 | 9/2006 | Khachin et al. |
| 7,112,217 B1 | 9/2006 | Kugler et al. |
| 7,118,600 B2 | 10/2006 | Dua et al. |
| 7,125,419 B2 | 10/2006 | Sequin et al. |
| 7,128,073 B1 | 10/2006 | van der Burg et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,659 B2 | 12/2006 | Jones |
| 7,147,660 B2 | 12/2006 | Chobotov et al. |
| 7,156,869 B1 | 1/2007 | Pacetti |
| 7,156,871 B2 | 1/2007 | Jones et al. |
| 7,160,317 B2 | 1/2007 | McHale et al. |
| 7,169,165 B2 | 1/2007 | Belef et al. |
| 7,172,575 B2 | 2/2007 | El-Nounou et al. |
| 7,172,617 B2 | 2/2007 | Colgan et al. |
| 7,175,607 B2 | 2/2007 | Lim et al. |
| 7,179,273 B1 | 2/2007 | Palmer et al. |
| 7,179,276 B2 | 2/2007 | Barry et al. |
| 7,179,284 B2 | 2/2007 | Khosravi et al. |
| 7,182,774 B2 | 2/2007 | Barry et al. |
| 7,195,648 B2 | 3/2007 | Jones et al. |
| 7,201,769 B2 | 4/2007 | Jones et al. |
| 7,201,770 B2 | 4/2007 | Johnson et al. |
| 7,223,284 B2 | 5/2007 | Khosravi et al. |
| 7,232,432 B2 | 6/2007 | Fulton, III et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,264,628 B2 | 9/2007 | Jones et al. |
| 7,270,674 B2 | 9/2007 | Jones et al. |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,123 B2 | 11/2007 | Jones et al. |
| 7,294,147 B2 | 11/2007 | Hartley |
| 7,300,458 B2 | 11/2007 | Henkes et al. |
| 7,303,572 B2 | 12/2007 | Melsheimer et al. |
| 7,306,619 B1 | 12/2007 | Palmer |
| 7,306,622 B2 | 12/2007 | Jones et al. |
| 7,309,345 B2 | 12/2007 | Wallace |
| 7,309,351 B2 | 12/2007 | Escamilla et al. |
| 7,311,726 B2 | 12/2007 | Mitelberg et al. |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,550 B2 | 3/2008 | Carrison et al. |
| 7,344,556 B2 | 3/2008 | Seguin et al. |
| 7,344,558 B2 | 3/2008 | Lorenzo et al. |
| 7,351,255 B2 | 4/2008 | Andreas |
| 7,354,455 B2 | 4/2008 | Stinson |
| 7,357,809 B2 | 4/2008 | Jones et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,402,169 B2 | 7/2008 | Killion et al. |
| 7,407,509 B2 | 8/2008 | Greenberg |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,481,821 B2 | 1/2009 | Fogarty et al. |
| 7,485,122 B2 | 2/2009 | Teoh |
| 7,494,474 B2 | 2/2009 | Richardson et al. |
| 7,510,565 B2 | 3/2009 | Gilson et al. |
| 7,517,352 B2 | 4/2009 | Evans et al. |
| 7,524,319 B2 | 4/2009 | Dubrul |
| 7,534,252 B2 | 5/2009 | Sepetka et al. |
| 7,549,974 B2 | 6/2009 | Nayak |
| 7,553,314 B2 | 6/2009 | Khachin et al. |
| 7,553,321 B2 | 6/2009 | Litzenberg et al. |
| 7,582,101 B2 | 9/2009 | Jones et al. |
| 7,618,434 B2 | 11/2009 | Santra et al. |
| 7,640,952 B2 | 1/2010 | Khachin et al. |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 | 7/2010 | Phung et al. |
| 7,780,694 B2 | 8/2010 | Palmer et al. |
| 7,833,240 B2 | 11/2010 | Okushi et al. |
| 7,972,342 B2 | 7/2011 | Gandhi et al. |
| 7,976,560 B2 | 7/2011 | Denison et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 8,357,179 B2 | 1/2013 | Grandfield et al. |
| 8,425,549 B2 | 4/2013 | Lenker et al. |
| 8,679,142 B2 | 3/2014 | Slee et al. |
| 8,926,680 B2 * | 1/2015 | Ferrara ............ A61B 17/12022 623/1.11 |
| 8,940,003 B2 | 1/2015 | Slee et al. |

(56) References Cited

U.S. PATENT DOCUMENTS

| | | |
|---|---|---|
| 9,078,682 B2 | 7/2015 | Lenker et al. |
| 9,161,766 B2 | 10/2015 | Slee et al. |
| 2001/0000797 A1 | 5/2001 | Mazzocchi |
| 2001/0003801 A1 | 6/2001 | Strecker |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0041899 A1 | 11/2001 | Foster |
| 2001/0044633 A1 | 11/2001 | Klint |
| 2001/0044647 A1 | 11/2001 | Pinchuk et al. |
| 2001/0044649 A1 | 11/2001 | Vallana et al. |
| 2001/0047202 A1 | 11/2001 | Slaikeu et al. |
| 2001/0051823 A1 | 12/2001 | Khosravi et al. |
| 2001/0053929 A1 | 12/2001 | Vonesh et al. |
| 2002/0004681 A1 | 1/2002 | Teoh et al. |
| 2002/0007210 A1 | 1/2002 | Chouinard et al. |
| 2002/0016564 A1 | 2/2002 | Courtney et al. |
| 2002/0016624 A1 | 2/2002 | Patterson et al. |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | McGuckin et al. |
| 2002/0087209 A1 | 7/2002 | Edwin et al. |
| 2002/0091355 A1 | 7/2002 | Hayden |
| 2002/0095141 A1 | 7/2002 | Belef et al. |
| 2002/0143387 A1 | 10/2002 | Soetikno et al. |
| 2002/0161377 A1 | 10/2002 | Rabkin |
| 2002/0169458 A1 | 11/2002 | Connors |
| 2002/0183831 A1 | 12/2002 | Rolando et al. |
| 2002/0193868 A1 | 12/2002 | Mitelberg et al. |
| 2002/0198588 A1 | 12/2002 | Armstrong et al. |
| 2003/0004536 A1 | 1/2003 | Boylan et al. |
| 2003/0023230 A1 | 1/2003 | Lewis et al. |
| 2003/0023299 A1 | 1/2003 | Amplatz et al. |
| 2003/0032941 A1 | 2/2003 | Boyle et al. |
| 2003/0032977 A1 | 2/2003 | Brady |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle et al. |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0199921 A1 | 10/2003 | Palmer et al. |
| 2003/0204202 A1 | 10/2003 | Palmer et al. |
| 2003/0212430 A1 | 11/2003 | Bose et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0010308 A1 | 1/2004 | Zafrir-Pachter et al. |
| 2004/0019322 A1 | 1/2004 | Hoffmann |
| 2004/0026942 A1 | 2/2004 | Kessler et al. |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078050 A1 | 4/2004 | Monstadt et al. |
| 2004/0078071 A1 | 4/2004 | Escamilla et al. |
| 2004/0079429 A1 | 4/2004 | Miller et al. |
| 2004/0088002 A1 | 5/2004 | Boyle et al. |
| 2004/0098025 A1 | 5/2004 | Sepetka et al. |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0153117 A1 | 8/2004 | Clubb et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0021125 A1 | 1/2005 | Stack et al. |
| 2005/0033334 A1 | 2/2005 | Santra et al. |
| 2005/0033348 A1 | 2/2005 | Sepetka et al. |
| 2005/0033349 A1 | 2/2005 | Jones et al. |
| 2005/0033409 A1 | 2/2005 | Burke et al. |
| 2005/0038447 A1 | 2/2005 | Huffmaster |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0055047 A1 | 3/2005 | Greenhalgh |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0090888 A1 | 4/2005 | Hines et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman et al. |
| 2005/0125023 A1 | 6/2005 | Bates et al. |
| 2005/0126979 A1 | 6/2005 | Lowe et al. |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0165441 A1 | 7/2005 | McGuckin et al. |
| 2005/0165442 A1 | 7/2005 | Thinnes et al. |
| 2005/0177228 A1 | 8/2005 | Solem et al. |
| 2005/0187612 A1 | 8/2005 | Edwin |
| 2005/0192661 A1 | 9/2005 | Griffen et al. |
| 2005/0209673 A1 | 9/2005 | Shaked |
| 2005/0209675 A1 | 9/2005 | Ton et al. |
| 2005/0209678 A1 | 9/2005 | Henkes et al. |
| 2005/0216050 A1 | 9/2005 | Sepetka et al. |
| 2005/0222583 A1 | 10/2005 | Cano et al. |
| 2005/0222607 A1 | 10/2005 | Palmer et al. |
| 2005/0222676 A1 | 10/2005 | Shanley et al. |
| 2005/0267570 A1 | 12/2005 | Shadduck |
| 2005/0277978 A1 | 12/2005 | Greenhalgh |
| 2006/0020285 A1 | 1/2006 | Niermann |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson et al. |
| 2006/0052797 A1 | 3/2006 | Kanamaru |
| 2006/0052816 A1 | 3/2006 | Bates et al. |
| 2006/0058833 A1 | 3/2006 | VanCamp et al. |
| 2006/0058836 A1 | 3/2006 | Bose et al. |
| 2006/0058838 A1 | 3/2006 | Bose et al. |
| 2006/0074480 A1 | 4/2006 | Bales et al. |
| 2006/0085065 A1 | 4/2006 | Krause et al. |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122643 A1 | 6/2006 | Wasicek |
| 2006/0122685 A1 | 6/2006 | Bonsignore |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0195118 A1 | 8/2006 | Richardson |

(56) References Cited

U.S. PATENT DOCUMENTS

| | | |
|---|---|---|
| 2006/0195172 A1 | 8/2006 | Luo et al. |
| 2006/0200048 A1 | 9/2006 | Furst et al. |
| 2006/0200221 A1 | 9/2006 | Malewicz |
| 2006/0224179 A1 | 10/2006 | Kucharczyk et al. |
| 2006/0224180 A1 | 10/2006 | Anderson et al. |
| 2006/0229645 A1 | 10/2006 | Bonnette et al. |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0287701 A1 | 12/2006 | Pal |
| 2006/0287704 A1 | 12/2006 | Hartley et al. |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru et al. |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135826 A1 | 6/2007 | Zaver et al. |
| 2007/0135888 A1 | 6/2007 | Khosravi et al. |
| 2007/0141036 A1 | 6/2007 | Gorrochategui Barrueta et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0179513 A1 | 8/2007 | Deutsch |
| 2007/0185501 A1 | 8/2007 | Martin et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski et al. |
| 2007/0198029 A1 | 8/2007 | Martin et al. |
| 2007/0198030 A1 | 8/2007 | Martin et al. |
| 2007/0198075 A1 | 8/2007 | Levy |
| 2007/0203452 A1 | 8/2007 | Mehta |
| 2007/0203559 A1 | 8/2007 | Freudenthal et al. |
| 2007/0208367 A1 | 9/2007 | Fiorella |
| 2007/0208371 A1 | 9/2007 | French et al. |
| 2007/0219621 A1 | 9/2007 | Hartley et al. |
| 2007/0225749 A1 | 9/2007 | Martin et al. |
| 2007/0225794 A1 | 9/2007 | Thramann et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288034 A1 | 12/2007 | MacCollum et al. |
| 2007/0288037 A1 | 12/2007 | Cheng et al. |
| 2007/0288038 A1 | 12/2007 | Bimbo |
| 2007/0288054 A1 | 12/2007 | Tanaka et al. |
| 2007/0288080 A1 | 12/2007 | Maccollum et al. |
| 2007/0288083 A1 | 12/2007 | Hines |
| 2007/0293846 A1 | 12/2007 | von Oepen et al. |
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt et al. |
| 2008/0058724 A1 | 3/2008 | Wallace |
| 2008/0071178 A1 | 3/2008 | Greenland et al. |
| 2008/0077175 A1 | 3/2008 | Palmer |
| 2008/0082107 A1 | 4/2008 | Miller et al. |
| 2008/0082159 A1 | 4/2008 | Tseng et al. |
| 2008/0086196 A1 | 4/2008 | Truckai et al. |
| 2008/0097495 A1 | 4/2008 | Feller, III et al. |
| 2008/0103477 A1 | 5/2008 | Jones |
| 2008/0103585 A1 | 5/2008 | Monstadt et al. |
| 2008/0109063 A1 | 5/2008 | Hancock et al. |
| 2008/0109067 A1 | 5/2008 | Caro et al. |
| 2008/0114439 A1 | 5/2008 | Ramaiah et al. |
| 2008/0114445 A1 | 5/2008 | Melsheimer et al. |
| 2008/0119888 A1 | 5/2008 | Huffmaster |
| 2008/0125855 A1 | 5/2008 | Henkes et al. |
| 2008/0140107 A1 | 6/2008 | Bei et al. |
| 2008/0140181 A1 | 6/2008 | Reynolds et al. |
| 2008/0147100 A1 | 6/2008 | Wallace |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0183185 A1 | 7/2008 | Miller et al. |
| 2008/0183198 A1 | 7/2008 | Sepetka et al. |
| 2008/0188865 A1 | 8/2008 | Miller et al. |
| 2008/0195140 A1 | 8/2008 | Myla et al. |
| 2008/0200946 A1 | 8/2008 | Braun et al. |
| 2008/0208319 A1 | 8/2008 | Rabkin et al. |
| 2008/0221554 A1 | 9/2008 | O'Connor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1 | 9/2008 | Snow et al. |
| 2008/0243229 A1 | 10/2008 | Wallace et al. |
| 2008/0243232 A1 | 10/2008 | Hegg et al. |
| 2008/0247943 A1 | 10/2008 | Lanza et al. |
| 2008/0249598 A1 | 10/2008 | Sherry |
| 2008/0255678 A1 | 10/2008 | Cully et al. |
| 2008/0262506 A1 | 10/2008 | Griffin et al. |
| 2008/0262528 A1 | 10/2008 | Martin |
| 2008/0262532 A1 | 10/2008 | Martin |
| 2008/0262592 A1 | 10/2008 | Jordan et al. |
| 2008/0269774 A1 | 10/2008 | Garcia et al. |
| 2008/0269868 A1 | 10/2008 | Bei et al. |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0125053 A1 | 5/2009 | Ferrera et al. |
| 2009/0163851 A1 | 6/2009 | Holloway et al. |
| 2009/0192455 A1 | 7/2009 | Ferrera et al. |
| 2009/0275974 A1 | 11/2009 | Marchand et al. |
| 2009/0292297 A1 | 11/2009 | Ferrere |
| 2009/0299393 A1 | 12/2009 | Martin et al. |

(56) References Cited

U.S. PATENT DOCUMENTS

| | | |
|---|---|---|
| 2010/0022951 A1 | 1/2010 | Ferrera et al. |
| 2010/0100106 A1 | 4/2010 | Ferrera |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0299911 A1 | 12/2010 | Gianotti et al. |
| 2010/0318097 A1 | 12/2010 | Ferrera et al. |
| 2011/0009875 A1 | 1/2011 | Grandfield et al. |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065600 A1 | 3/2012 | Ashmead et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0083868 A1 | 4/2012 | Shrivastava et al. |
| 2012/0089216 A1 | 4/2012 | Rapaport et al. |
| 2012/0116443 A1 | 5/2012 | Ferrera et al. |
| 2014/0343596 A1 | 11/2014 | Slee et al. |
| 2015/0157346 A1 | 6/2015 | Ferrera et al. |
| 2015/0359549 A1 | 12/2015 | Lenker et al. |

FOREIGN PATENT DOCUMENTS

| | | |
|---|---|---|
| CN | 101061970 A | 10/2007 |
| DE | 2804058 A1 | 8/1978 |
| DE | 2821048 B1 | 11/1979 |
| DE | 8435489 U1 | 8/1986 |
| DE | 19703482 A1 | 8/1998 |
| DE | 10010840 A1 | 9/2001 |
| EP | 201466 A2 | 11/1986 |
| EP | 484468 A1 | 5/1992 |
| EP | 629125 A1 | 12/1994 |
| EP | 0321912 B1 | 2/1995 |
| EP | 707830 A1 | 4/1996 |
| EP | 719522 A1 | 7/1996 |
| EP | 726745 A1 | 8/1996 |
| EP | 737450 A1 | 10/1996 |
| EP | 739606 A1 | 10/1996 |
| EP | 750886 A1 | 1/1997 |
| EP | 752236 A1 | 1/1997 |
| EP | 800790 A2 | 10/1997 |
| EP | 803230 A2 | 10/1997 |
| EP | 804904 A1 | 11/1997 |
| EP | 804905 A1 | 11/1997 |
| EP | 804906 A2 | 11/1997 |
| EP | 807410 A2 | 11/1997 |
| EP | 820729 A1 | 1/1998 |
| EP | 826341 A1 | 3/1998 |
| EP | 826342 A1 | 3/1998 |
| EP | 832606 A1 | 4/1998 |
| EP | 861634 A2 | 9/1998 |
| EP | 914803 A1 | 5/1999 |
| EP | 964659 A1 | 12/1999 |
| EP | 1000590 A1 | 5/2000 |
| EP | 1005837 A2 | 6/2000 |
| EP | 1009295 A1 | 6/2000 |
| EP | 1009296 A1 | 6/2000 |
| EP | 1225844 A2 | 7/2002 |
| EP | 1266639 A2 | 12/2002 |
| EP | 1266640 A2 | 12/2002 |
| EP | 1323385 A2 | 7/2003 |
| EP | 1329196 A1 | 7/2003 |
| EP | 1351626 A2 | 10/2003 |
| EP | 1366720 A1 | 12/2003 |
| EP | 1400219 A1 | 3/2004 |
| EP | 1437097 A1 | 7/2004 |
| EP | 2257248 B1 | 10/2011 |
| EP | 2301450 B1 | 11/2011 |
| EP | 2417919 A2 | 2/2012 |
| EP | 2254485 B1 | 8/2017 |
| FR | 2343488 A1 | 10/1977 |
| GB | 2020557 A | 11/1979 |
| JP | 2095359 | 4/1990 |
| JP | 02255157 A | 10/1990 |
| JP | 6-246004 | 9/1994 |
| JP | 8-033719 A | 2/1996 |
| JP | 2975584 B2 | 11/1999 |
| JP | 2001-190686 A | 7/2001 |
| JP | 2001178830 A | 7/2001 |
| JP | 2003-033359 A | 2/2003 |
| JP | 2004016668 A | 1/2004 |
| JP | 2005532887 A | 11/2005 |
| JP | 2006026423 A | 2/2006 |
| JP | 2006-075233 A | 3/2006 |
| JP | 2006-094876 A | 4/2006 |
| JP | 2006095095 A | 4/2006 |
| JP | 2007-185363 A | 7/2007 |
| JP | 2007-222658 A | 9/2007 |
| JP | 2007-236471 A | 9/2007 |
| WO | WO-94/03127 A1 | 2/1994 |
| WO | WO-96/17634 A2 | 6/1996 |
| WO | WO-96/28116 A1 | 9/1996 |
| WO | WO-97/04711 A1 | 2/1997 |
| WO | WO-98/25656 A3 | 10/1998 |
| WO | WO-98/55173 A1 | 12/1998 |
| WO | WO-98/55175 A1 | 12/1998 |
| WO | WO-99/16382 A2 | 4/1999 |
| WO | WO-99/23976 A1 | 5/1999 |
| WO | WO-99/25252 A1 | 5/1999 |
| WO | WO-99/29264 A1 | 6/1999 |
| WO | WO-99/44542 A2 | 9/1999 |
| WO | WO-99/48429 A1 | 9/1999 |
| WO | WO-99/48440 A1 | 9/1999 |
| WO | WO-00/012166 A1 | 3/2000 |
| WO | WO-2000/32265 A1 | 6/2000 |
| WO | WO-2000/53120 | 9/2000 |
| WO | WO-00/59405 A1 | 10/2000 |
| WO | WO-2001/008743 A1 | 2/2001 |
| WO | WO-2001/36034 A2 | 2/2001 |
| WO | WO-01/32099 A2 | 5/2001 |
| WO | WO-2001/034041 | 5/2001 |
| WO | WO-01/45566 A1 | 6/2001 |
| WO | WO-2001/45569 A1 | 6/2001 |
| WO | WO-01/72240 A1 | 10/2001 |
| WO | WO-01/93780 A2 | 12/2001 |
| WO | WO-02/54980 A2 | 7/2002 |
| WO | WO-2003/017823 A2 | 3/2003 |
| WO | WO-2004008991 A1 | 1/2004 |
| WO | WO-2003/011188 A9 | 7/2004 |
| WO | WO-2004/093696 A1 | 11/2004 |

(56) References Cited

FOREIGN PATENT DOCUMENTS

| WO | WO-2006/052439 | A1 | 5/2006 |
|---|---|---|---|
| WO | WO-2007/089897 | | 8/2007 |
| WO | WO-2007/121005 | A1 | 10/2007 |
| WO | WO-2008/117256 | A2 | 5/2008 |
| WO | WO-2008063156 | A2 | 5/2008 |
| WO | WO-2008/117257 | A2 | 10/2008 |
| WO | WO-2008/124728 | A1 | 10/2008 |
| WO | WO-2009/067629 | A2 | 5/2009 |
| WO | WO-2009/086154 | A2 | 7/2009 |
| WO | WO-2009/105710 | A1 | 8/2009 |
| WO | WO-2009/114046 | A2 | 9/2009 |
| WO | WO-2009/124288 | A1 | 10/2009 |
| WO | WO-2009/126747 | A1 | 10/2009 |
| WO | WO-2010/010545 | A1 | 1/2010 |
| WO | WO-2010/023671 | A2 | 3/2010 |
| WO | WO-2010/046897 | A1 | 4/2010 |
| WO | WO-2010/049121 | A2 | 5/2010 |
| WO | WO-2010/062363 | A1 | 6/2010 |
| WO | WO-2010/102307 | A1 | 9/2010 |
| WO | WO-2010/115642 | A1 | 10/2010 |
| WO | WO-2010/121037 | A1 | 10/2010 |
| WO | WO-2010/121049 | A2 | 10/2010 |
| WO | WO-2011/054531 | A2 | 5/2011 |
| WO | WO-2011/095352 | A1 | 8/2011 |
| WO | WO-2011/133486 | A1 | 10/2011 |
| WO | WO-2011/135556 | | 11/2011 |
| WO | WO-2011/144336 | | 11/2011 |
| WO | WO-2011/147567 | | 12/2011 |
| WO | WO-2012/009675 | | 1/2012 |
| WO | WO-2012/025245 | | 3/2012 |
| WO | WO-2012/025247 | | 3/2012 |

OTHER PUBLICATIONS

"Penumbra, Inc Enrolls First Patients in PULSE Clinical Trial to Evaluate a Fully Retrievable, Dense Mesh Temporary Stent for Immediate Flow Restoration in Interventional Acute Ischemic Stroke Treatment," Business Wire, Nov. 1, 2010, <http://wwwbusinesswirecom/news/home/d0101101006991/en/Penumbra-Enrolls-Patients-PULSE-Clinical-Trial-Evaluate>.
Doerfler, et al, "A Novel Flexible, Retrievable Endovascular Stent System for Small-Vessel Anatomy: Preliminary in Vivo Data," Am J Neuroradiol vol. 26, pp. 862-868 (Apr. 2005).
Duerig, et al An Overview of Superelastic Stent Design Min Invas Ther & Allied Technol 2000: 9(3/4) 235-246.
Henkes, et al, "A Microcatheter-Delivered Highly-Flexible and Fully-Retrievable Stent, Specifically Designed for Intracranial Use," Interventional Neuroradiology, vol. 9, pp. 391-393 (Dec. 2003).
Kelly, et al, Recanalization of an Acute Cerebral Artery Occlusion Using a Self-Expanding, Reconstrainable, Intracranial Microstent as a Temporary Endovascular Bypass; AHA Journal, Jun. 2008 edition.
Lavallee, et al, Stent-Assisted Endovascular Thrombolysis Versus Intravenous Thrombolysis in Internal Carotid Artery Dissection with Tandem Internal Carotid and Middle Cerebral Artery Occlusion, AHA 2007.
Levy, et al, Self-Expanding Stents for Recanalization of Acute Cerebrovascular Occulsions; AJNR May 28, 2007.
Liebig, et al, "A novel self-expanding fully retrievable intracranial stent (SOLO): experience in nine procedures of stent-assisted aneurysm coil occlusion," Neuroradiology vol. 48, pp. 471-478 (Jul. 2006).
Micro Therapeutics, Inc, DBA EV3 Neurovascular, Inc, Fully deployable Completely retrievable, Solitaire AB, Neurovascular Remodeling Device Mar. 2008.
Micro Therapeutics, Inc, DBA EV3 Neurovascular, Inc, Solitaire FR Revascularization Device, Instructions for Use, Rev Mar. 2009.
Pelz, et al, Advances in Interventional Neuroradiology 2007; American Heart Association Journal, Nov. 2007 edition.
Robertson, Stroke device startup lands National Science Foundation grant, Sacramento Business Journal, Oct. 23, 2009, Sacramento, California.
Sauvegeau, et al Middle Cerebral Artery Stenting for Acute Ischemic Stroke After Unsuccessful Merci Retrieval; Special Technical Report; Neurosurgery 60:701-706, 2007.
Wakhloo, et al, "Retrievable Closed Cell Intracranial Stent for Foreign Body and Clot Removal," Neurosurgery, May 5, 2008.
Yavuz, et al, "Immediate and midterm follow-up results of using an electrodetachable, fully retrievable SOLO stent system in the endovascular coil occlusion of wide-necked cerebral aneurysms," J Neurosurg vol. 107, pp. 49-55 (Jul. 2007).
Schumacher, H, "Endovascular Mechanical Thrombectomy of an Occluded Superior Division Branch of the Left MCA for Acute Cardioembolic Stroke," Cardiovascular and Interventional Radiology, Jun. 2003 26(3) pp. 305-308.
Nesbit, G, "New and Future Endovascular Treatment Strategies for Acute Ischemic Stroke," Journal of Vascular and Interventional Radiology, Jan. 2004 15(1) pp. S103-S110.
Imai, K, "Clot Removal Therapy by Aspiration and Extraction for Acute Embolic Carotid Occlusion," American Journal of Neuroradiology, Aug. 2006, vol. 27, pp. 1521-1527.
Wildberger, J, "Percutaneous Venous Thrombectomy Using the Arrow-Trerotola Percutaneous Thrombolytic Device (PTD) with Temporary Caval Filtration: In Vitro Investigations," Cardiovascular and Interventional Radiology, Mar. 2005 28(2) pp. 221-227.
Castano, C, "Use of the New Solitaire (TM) AB Device for Mechanical Thrombectomy when Merci Clot Retriever Has Failed to Remove the Clot A Case Report," Interventional Neuroradiology, Jul. 2009 15(2) pp. 209-214.
Ev3 Solitaire Brochure R2 dated Jan. 12, 2009.
Ev3 Solitaire AB Instructions for Use (IFU) dated Dec. 2007 The first commercial sale of the products numbered SAB-4-15 and SAB 4 20, referenced in the ev3 Solitaire AB IFU dated Dec. 2007, occurred on Jan. 4, 2008.
J Gralla, et al, "A Dedicated Animal Model for Mechanical Thrombectomy in Acute Stroke," ANJR 27:1357-61, Jun.-Jul. 2006.
J Gralla, et al, "Mechanical Thrombectomy for Acute Ischemic Stroke," Stroke 37:3019-3024, Dec. 2006.
V Marder, et al, "Analysis of Thrombi Retrieved From Cerebral Arteries of Patients With Acute Ischemic Stroke," Stroke 37:2086-2093, Aug. 2006.
T Massoud, et al, "Histopathologic Characteristics of a Chronic Arteriovenous Malformation in a Swine Model: Preliminary Study," AJNR 21:1268-1276, Aug. 2000.
Thomas Liebig, et al (p. 5) and "Multimodal endovascular treatment of ischemic stroke by mechanical thrombectomy; a two center / two years experience" Z Vajda, et al (p. 6).
H Henkes, et al, "Endovascular acute ischemic stroke treatment using the self-expanding and fully retrievable Solitaire stent", poster exhibition displayed on one or both of Feb. 18 and 19, 2009, at the International Stroke Conference, San Diego, California.
Abstracts from the 2009 International Stroke Conference, Stroke, 2009; 40, pp. e247-e248, originally published online Feb. 16, 2009.
Opposition Filed in EP 2254485.
Opposition (English Translation) in European Patent 2254485, dated May 30, 2018.
Reply to Opposition in European Patent 2254485, dated Oct. 29, 2018.
File History in Australian Patent Application No. 2016277687.
Summons to attend oral proceedings pursuant to Rule 115(1) EPC dated Mar. 1, 2019 in EP Application No. 09711843.4.

\* cited by examiner

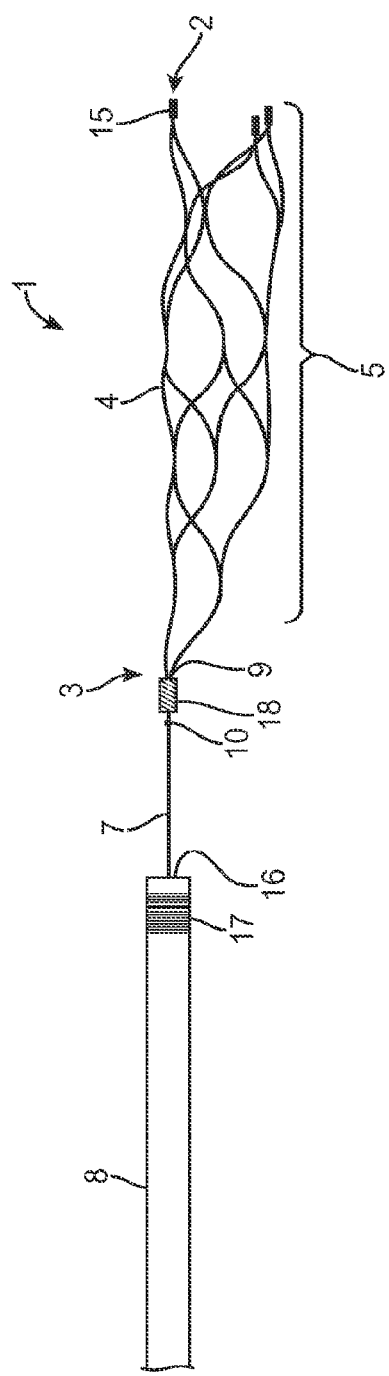
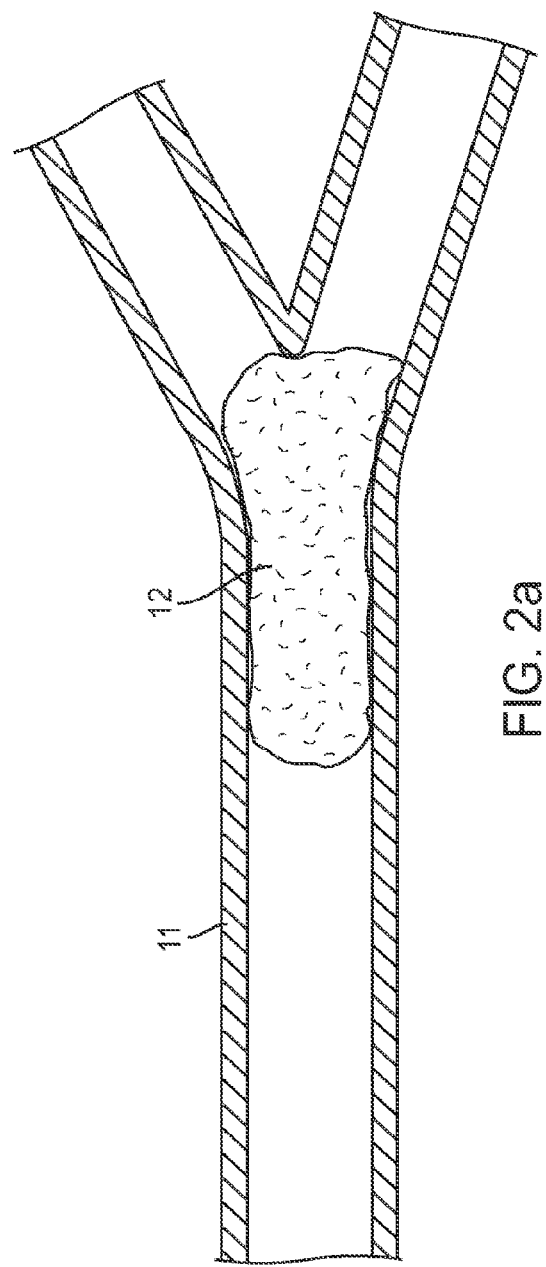
FIG. 1
FIG. 2a

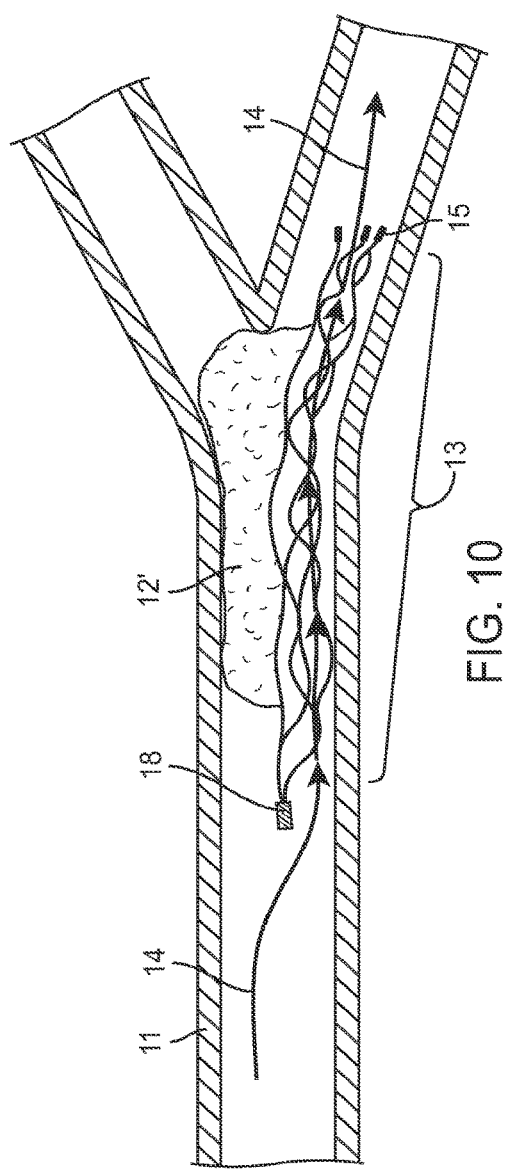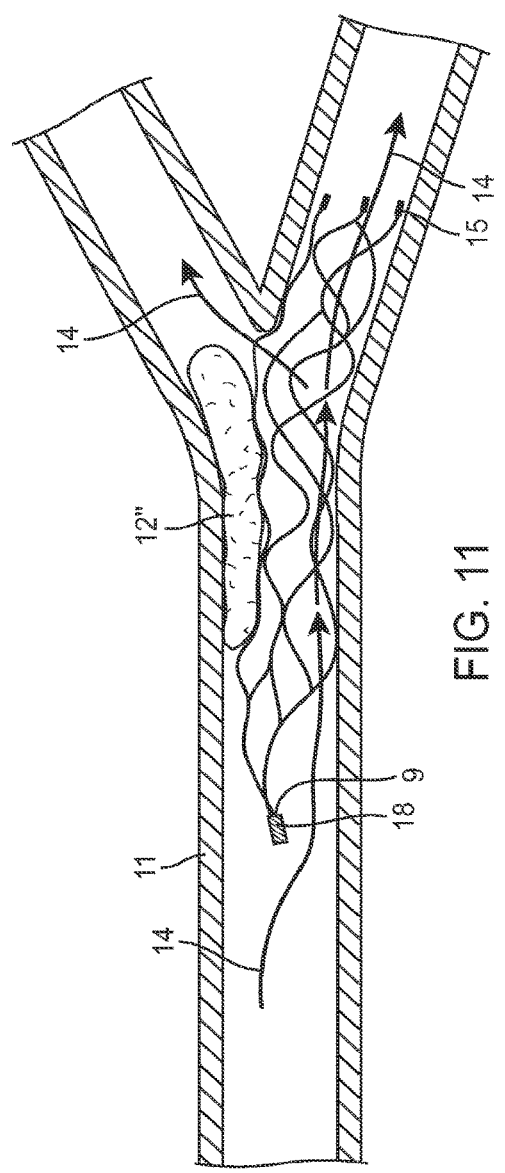

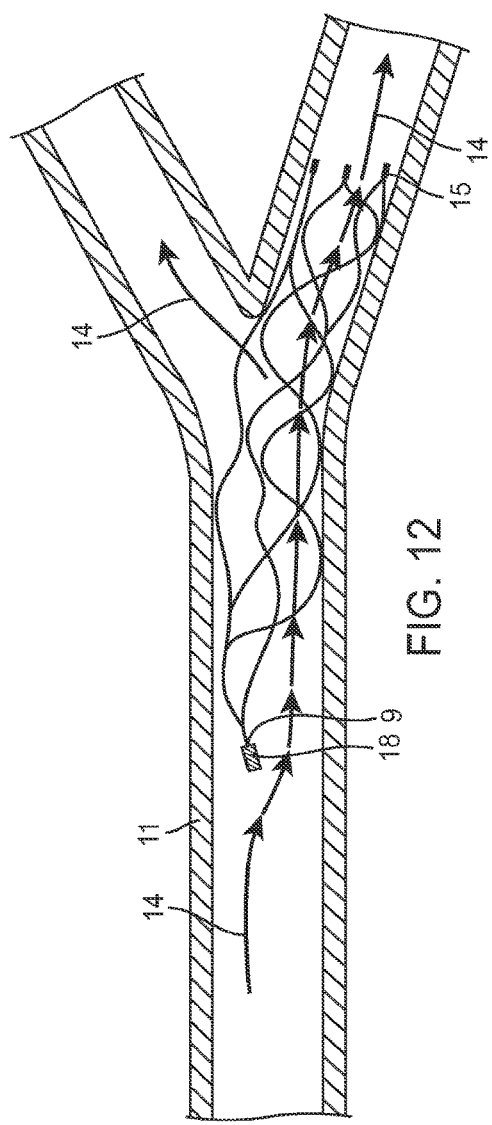
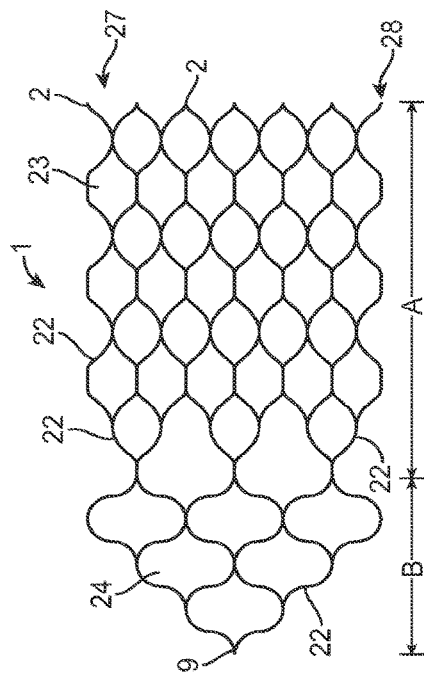

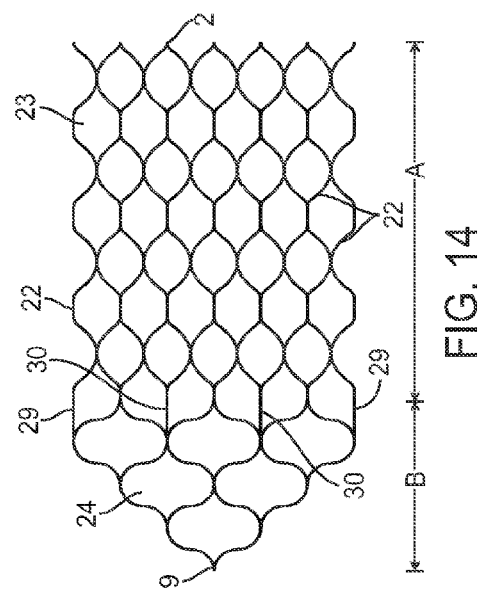
FIG. 14
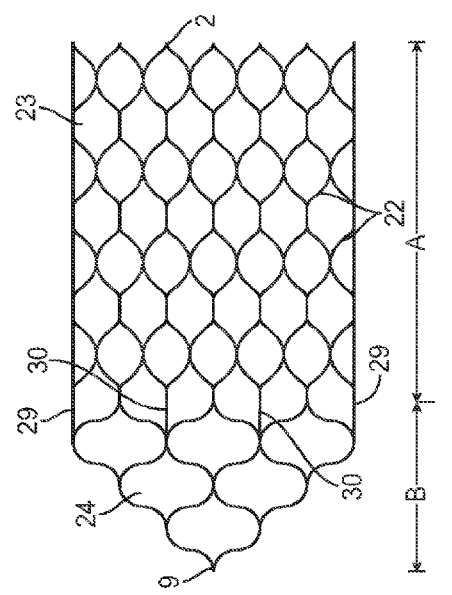
FIG. 15
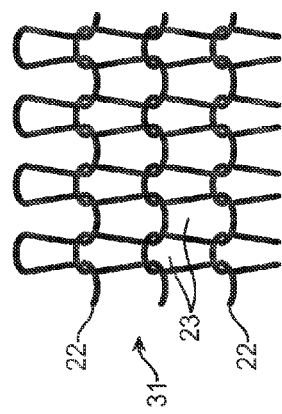
FIG. 16
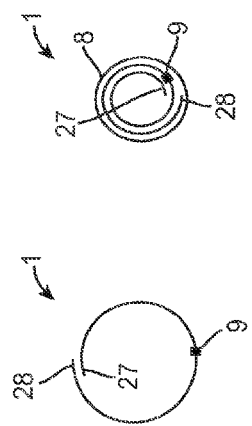
FIG. 17a
FIG. 17b

METHODS AND APPARATUS FOR FLOW RESTORATION

CROSS-REFERENCE TO RELATED APPLICATIONS

This application is a continuation of U.S. patent application Ser. No. 14/136,252, filed on Dec. 20, 2013, which is a continuation of U.S. patent application Ser. No. 13/678,464, filed on Nov. 15, 2012, which is a continuation of U.S. patent application Ser. No. 12/918,795, filed on Nov. 22, 2010, which is a U.S. National Phase under 35 U.S.C. § 371 of International Application No. PCT/US2009/034774, filed on Feb. 20, 2009, which claims the benefit under 35 U.S.C. § 119(e) of U.S. Provisional Application Ser. No. 61/030,838, filed on Feb. 22, 2008, each of which is hereby incorporated by reference in its entirety.

FIELD OF THE INVENTION

The present invention relates to methods and apparatus for quickly or immediately restoring blood flow in occluded blood vessels, particularly occluded cerebral arteries. Furthermore, the present invention relates to the application of such apparatus for thrombus removal and/or thrombus dissolution.

BACKGROUND OF THE INVENTION

Current technology for treating cerebral arteries occluded by thrombus may take hours to reestablish flow in the artery. Furthermore, known apparatus and methods for treating cerebral thrombus may be ineffective or only partially effective at resolving thrombus, and may additionally result in distal embolization or embolization of uninvolved arteries. The risk and degree of permanent neurological deficit increases rapidly with increased time from onset of symptoms to blood flow restoration.

SUMMARY OF THE INVENTION

The invention is directed to methods of restoring localized blood flow in a vascular site occluded with a thrombus. It is contemplated that the methods of the invention improve the speed and effectiveness of revascularization of cerebral arteries occluded by a thrombus.

In one embodiment, methods and apparatus are provided to create immediate (or restore) blood flow in the occluded artery upon deployment of the apparatus. In one aspect, a self-expandable apparatus is delivered to a site that is radially adjacent to the thrombus and the apparatus is expanded thereby restoring flow.

In another embodiment, the invention is directed to methods and apparatus that restore blood flow in the blood vessel that is occluded with a thrombus, with an associated increased efficiency in dislodging the thrombus from the vessel and removing the thrombus. In this embodiment, a self-expandable apparatus is delivered to a site that is radially adjacent to the thrombus and then expanded. The expanded apparatus then restores flow, which flow assists in disloding the thrombus from the vessel wall. In one embodiment, the apparatus enages the thrombus and the thrombus can then be removed from the site of occlusion.

In yet another embodiment, the invention is directed to methods and apparatus that restore blood flow in the occluded artery, with an associated increased efficiency in dissolving part or all of the thrombus from the vessel and optionally retrieval of the apparatus. In this embodiment, a self-expandable apparatus is delivered to a site that is radially adjacent to the thrombus and then expanded. Once expanded, the apparatus then restores flow to the occluded site and this increased flow may dissolve or partially or substantially dissolve the thrombus and the apparatus-thrombus mass is then removed from the formerly occluded site.

In still yet another embodiment, the invention is directed to methods and apparatus that restore blood flow in the occluded artery, with an associated increased efficiency in dissolving part or all of the thrombus from the vessel and implantation of a portion of the apparatus. In this embodiment, the apparatus engages (or implants in or integrates with) at least a portion of the thrombus providing a removable, integrated apparatus-thrombus mass. The removable, integrated apparatus-thrombus is removed from the site of occlusion.

In some embodiments, the method of the invention is directed to a method for imaging restoration of blood flow in a blood vessel occluded with a thrombus. This method comprises: a) acquiring an image of a self-expandable apparatus placed radially adjacent to a thrombus; and b) acquiring an image of expanding the apparatus thereby restoring blood flow.

In another embodiment, the method of the invention is directed to a method for imaging partially or substantially dissolving a thrombus lodged in a blood vessel. This method comprises: a) acquiring an image of a self-expandable apparatus placed radially adjacent to a thrombus; and b) acquiring an image of expanding the apparatus thereby increasing blood through the vessel wherein the increased blood flow partially or substantially dissolves the thrombus.

In still yet another embodiment, the method of invention is directed to a method for imaging dislodging a thrombus lodged in a blood vessel. This method comprises: a) acquiring an image of a self-expandable apparatus placed radially adjacent to a thrombus; b) acquiring an image of expanding the apparatus thereby engaging at least a portion of the thrombus; and c) acquiring an image of moving the apparatus distally or proximally thereby dislodging the thrombus.

A number of self-expandable apparatus are contemplated to be useful in the methods of the invention. In one embodiment, the apparatus is reversibly self-expandable. In another embodiment, the apparatus is fully retrievable or retractable. In one embodiment, the self-expandable apparatus comprises a mesh structure comprising a first plurality of mesh cells, the mesh structure having a proximal end and a distal end; a tapering portion comprising a second plurality of mesh cells, the tapering portion disposed toward the proximal end of the mesh structure; and a connection point, at which the tapering portion converges, located at a proximal end of the tapering portion, wherein the apparatus is preformed to assume a volume-enlarged form and, in the volume-enlarged form, takes the form of a longitudinally open tube tapering toward the connection point.

Another embodiment of the invention is a self-expandable apparatus for removal of a thrombus in a blood vessel, comprising: a mesh structure comprising a first plurality of mesh cells, the mesh structure having a proximal end and a distal end wherein said distal end of the mesh structure is configured to engage at least a portion of the thrombus to form a removable, integrated apparatus-thrombus mass; a tapering portion comprising a second plurality of mesh cells, the tapering portion disposed toward the proximal end of the mesh structure; and a connection point, at which the tapering portion converges, located at a proximal end of the tapering portion, wherein the apparatus is pre-formed to assume a volume-enlarged form and, in the volume-enlarged form, takes the form of a longitudinally open tube tapering toward the connection point.

It is contemplated that the distal end of the mesh structure is configured to assist in thrombus retrieval by providing increasing support to the mesh structure and by increasing thrombus retention.

In another embodiment of the invention is provided a removable, integrated apparatus-thrombus mass, comprising a thrombus at least partially engaged with an apparatus, wherein the apparatus comprises a mesh structure comprising a first plurality of mesh cells, the mesh structure having a proximal end and a distal end wherein said distal end of the mesh structure is configured to engage at least a portion of the thrombus; a tapering portion comprising a second plurality of mesh cells, the tapering portion disposed toward the proximal end of the mesh structure; and a connection point, at which the tapering portion converges, located at a proximal end of the tapering portion, wherein the apparatus is pre-formed to assume a volume-enlarged form and, in the volume-enlarged form, takes the form of a longitudinally open tube tapering toward the connection point.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1 shows an apparatus useful for the methods of the present invention.

FIG. 2a shows a target occlusion or thrombus to be treated by the present invention.

FIG. 3 is shown with the microcatheter 8 in phantom.

FIGS. 10, 11, and 12 show apparatus implantation methods according to the present invention.

FIG. 13 is an apparatus according to one embodiment of the present invention having a honeycomb structure.

FIG. 14 is another embodiment of a stent according to the present invention having a honeycomb structure.

FIG. 15 is a third embodiment of a stent according to the present invention having a honeycomb structure.

FIG. 16 is a warp-knitted structure as can be used for an apparatus according to the invention.

FIG. 17a and FIG. 17b is a schematic representation of an apparatus according to an embodiment of the present invention shown in its superimposed and in its volume-reduced shape.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications and patent applications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

Methods

The invention is directed to methods of restoring localized flow to an occluded vascular site. The vascular site, or blood vessel, can be occluded by a thrombus. The apparatus employed in the methods of the invention may be positioned at the vascular site with a microcatheter and optionally a guide catheter. The methods of the invention may employ a fully retrievable apparatus which is an improvement over the art which methods required the apparatus to be implanted permanently into the patient. When the apparatus is permanently placed in the patient, lifelong anticoagulant therapy for the patient is required. Therefore, it is contemplaed that by using a retrievable apparatus, lifelong anticoagulant therapy may be avoided.

Figure 2B:
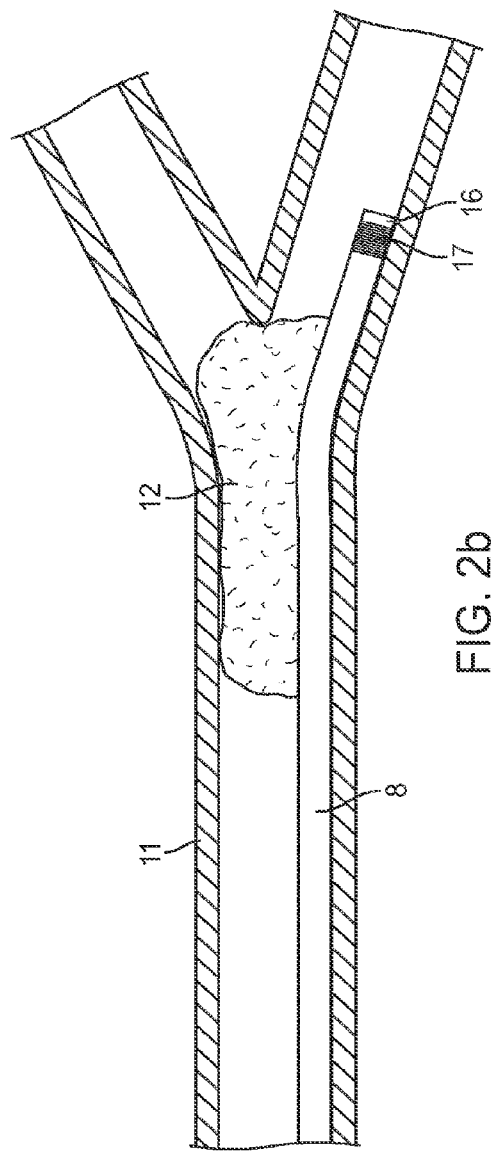
FIGS. 2b, 3, and 4 show placement methods according to the present invention.
Figure 3:
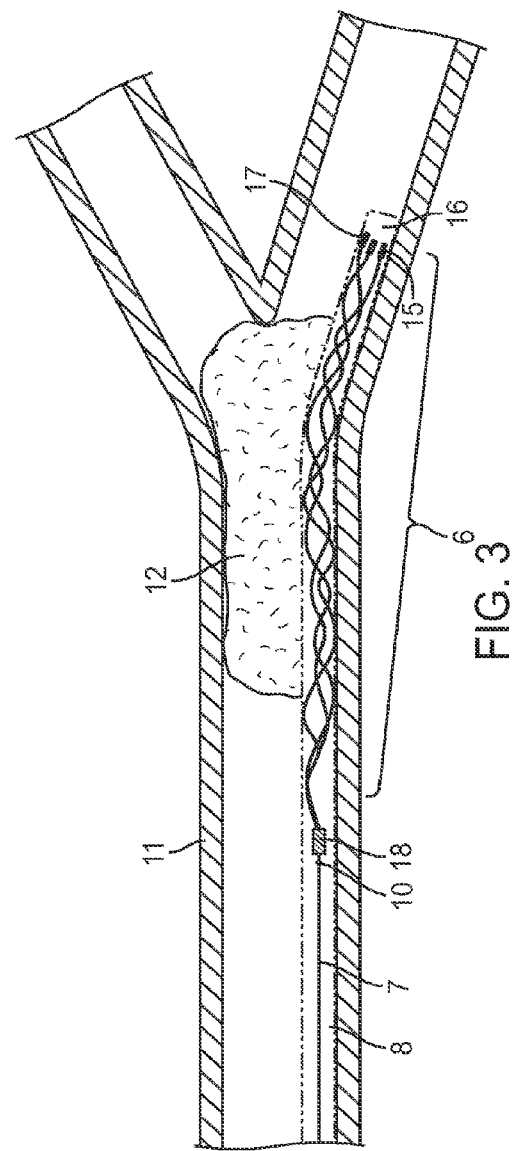

Methods and apparatus are provided to restore blood flow in cerebral arteries 11 occluded with thrombus 12 (FIG. 2a). Such methods utilize an apparatus having a self-expandable, optionally reversibly self-expandable, distal segment 1 including distal end 2, proximal end 3, and body portion 4 that is pre-formed to assume a superimposed structure 5 in an unconstrained condition but can be made to take on a volume-reduced form 6 making it possible to introduce it with a push wire 7 attached at the proximal end 3 and a microcatheter 8, with the distal segment 1 in its superimposed structure 5 assuming the form of a longitudinally open tube and having a mesh structure of interconnected strings or filaments or struts (FIGS. 1 and 3). In one embodiment, the distal segment 1 has a tapering structure at its proximal end 3 where the strings or filaments or struts converge at a connection point 9. The push wire 7 is preferably attached at or adjacent to the connection point 9. Such attachment 10 may be permanent or a releasable mechanism. The methods disclosed herein can be performed with the medical distal segment 1 (or apparatus or stent, of which all terms are used interchangeably) described in U.S. Pat. No. 7,300,458, which is incorporated herein in its entirety.

Figure 4:
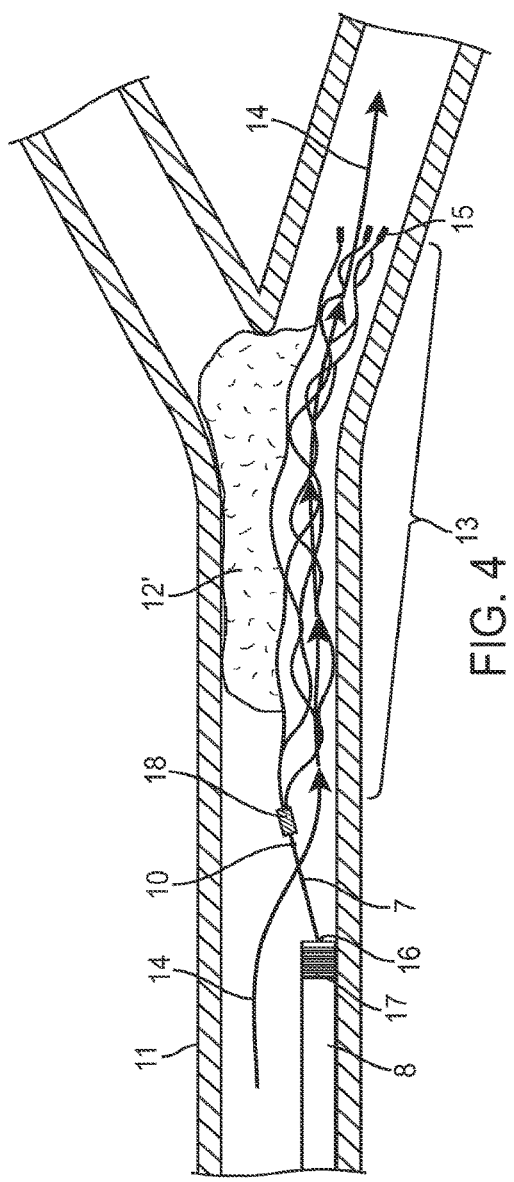

According to the present invention, the self-expandable distal segment 1 of the apparatus is positioned within a blood vessel 11 occluded by thrombus 12 in a volume-reduced form 6 by advancing it with the push wire 7 within a microcatheter 8 such that its proximal end 3 is upstream of the thrombus and its distal end 2 and is downstream of the thrombus and the body portion 4 is located radially adjacent to the thrombus 12 (FIGS. 1 and 3). As shown in FIG. 3, the distal end 2 of the distal segment 1 is positioned distal to the distal thrombus boundary and the proximal end 3 of the distal segment is positioned proximal of the proximal thrombus boundary. The distal segment 1 is held in a fixed position by holding the push wire 7 stationary while the distal segment 1 is released from its volume-reduced form 6 by withdrawing the microcatheter 8 proximally of the distal segment 1 (FIG. 4). The distal segment 1 assumes at least a portion of its superimposed structure 5 in its unconstrained condition 13 thereby expanding to bring at least part of the body portion into penetrating contact with the thrombus 12', exerting an outward radial force on the thrombus 12', reducing the cross-sectional area of the thrombus 12', and immediately re-establishing blood flow 14 through the blood vessel 11 past the thrombus 12'.

Also contemplated by this invention is administration of an effective amount of a clot-busting drug, such as, for example tissue plasminogen activator (tPA), to the site of the thrombus. Administration of this drug will act to further enhance dissolution of the clot.

This placement methodology expands the population of patients eligible for treatment over apparatus that require intravascular space distal to the reach of a microcatheter as the methodology of this invention places the distal segment 1 beyond the distal end of the thrombus 12. Additionally, this placement methodology expands the population of physicians that can successfully practice the method, as it is delivered with microcatheter technology already familiar to the user, and facilitates rapid placement of the apparatus. Immediately restoring blood flow 14 is a significant advantage over known apparatus and methods for treating cerebral arteries 11 occluded by thrombus 12 because known apparatus and methods may take hours to re-establish flow 14, and it is well established that the risk and degree of permanent neurological deficit increases rapidly with increased time from onset of symptoms to blood flow restoration.

In one embodiment thrombus removal methods and apparatus are provided that restore blood flow 14 in the occluded artery 11, with an increased efficiency in dislodging the thrombus 12' from the vessel coupled with removal of the thrombus 12' and apparatus from the patient. In a preferred embodiment, restoring blood flow 14 in the occluded artery 11 involves placing a microcatheter 8 such that the distal tip 16 of the microcatheter is beyond the distal end of the thrombus 12, wherein the distal tip 16 is from greater than about 0 millimeter (mm) to about 10 mm or more, or about 3 mm to about 5 mm (FIG. 2b) beyond the distal end of the thrombus 12. The self-expandable distal segment 1 is advanced within the microcatheter 8 in its reduced volume form 6 by the push wire 7 until its distal end 2 is just beyond the distal end of the thrombus 12 (FIG. 3).

Visualization of proper placement may be done by fluoroscopy. Specifically, this may be accomplished by aligning radiopaque markers 15 on the distal end of the distal segment with a distal radiopaque microcatheter marker 17 (FIG. 3). As mentioned above, this invention is also directed to various methods of acquiring images of the process. The method of imaging typically employed is fluoroscopy (which can confirm proper placement of the apparatus) or contrast injection (which can confirm blood flow restoration). However, a number of imaging methods known by those of skill in the art are also contemplated.

The distal segment 1 is then deployed within and across the thrombus 12' by holding the push wire 7 fixed while withdrawing the microcatheter 8 proximally until the distal segment 1 is released 13 (FIG. 4). One indication of full deployment is the visualization by the clinician that a radiopaque marker 18 defining the proximal end 3 of the distal segment 1 is aligned with, or distal of, the distal radiopaque microcatheter marker 17. Alternatively, the microcatheter 8 can be completely removed from the patient. Immediately upon distal segment 1 deployment 13, blood flow 14 is restored across the thrombus 12' and confirmation can be visualized via contrast injection. This is an indication of proper distal segment position relative to the thrombus 12' and vascular anatomy.

The apparatus can be used to remove the thrombus 12' after one of the following: a fixed amount of time has elapsed after deployment 13 of the distal segment 1, which may be from about 0 minutes to about 120 minutes or more; blood flow 14 across the thrombus 12' is observed to stop; a predetermined maximum amount of flow time has elapsed, whichever occurs first.

Figure 5:
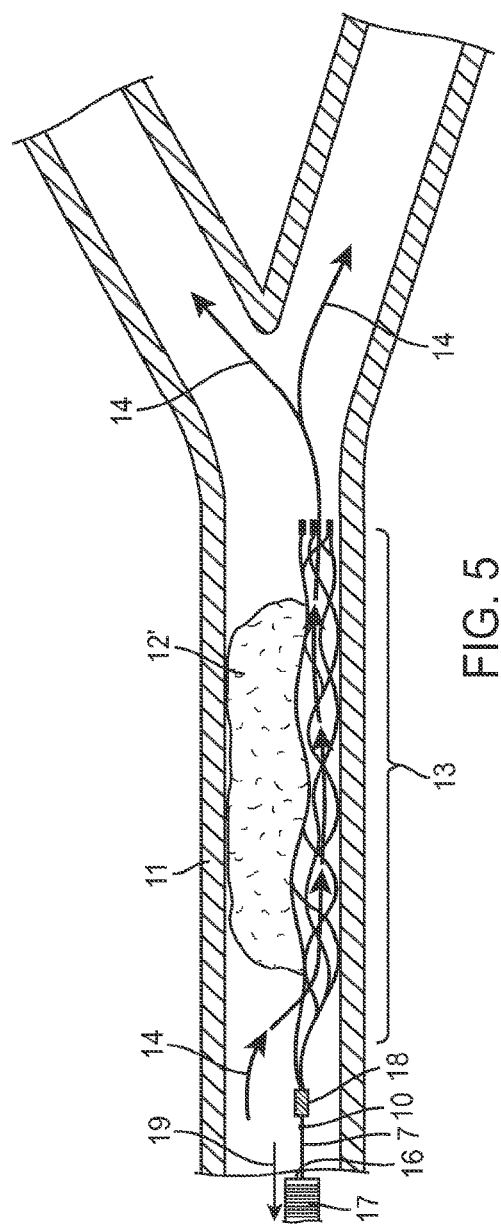
FIG. 5 shows thrombus dislodgement and mobilization according to the present invention.

Removing the thrombus 12' may be accomplished by any number of variations (FIG. 5). For example, as the distal tip of volume-reduced form 6 is moved beyond the thrombus, it will encounter less resistance to expansion and provide a greater radial force as compared to that portion engaging the thrombus as shown in FIG. 5. Thus distal tip 2 may expand beyond the thrombus 12' creating a distal tip 2 having a larger diameter than the diameter of the distal segment that is engaged by at least a portion of the thrombus. In some embodiments, this can be a hook-like distal configuration. Further structural modifications are described below that could be used to further aid in thrombus engagement and removal. Using the push wire 7, a pull force 19 of the deployed distal segment 13 will retract the thrombus back to the catheter as the hook-like configuration acts to snag the thrombus. Subsequent removal of the catheter will result in removal of the thrombus from the site of occlusion.

Prior to pulling the apparatus back, the microcatheter 8 can be manipulated in any of the following ways: the distal radiopaque microcatheter marker 17 can be left at or proximal to distal segment proximal radiopaque marker 18 or completely removed from patient; microcatheter 8 can be moved forward to a predetermined point relative to the distal segment 1, which may be: when the distal radiopaque microcatheter marker 17 is desirably aligned with the distal segment of proximal radiopaque marker 18; when the distal radiopaque microcatheter marker 17 is desirably aligned distal of the distal segment of proximal radiopaque marker 18, for example about 0.5 mm to about 10 mm or about 5 mm to about 10 mm; when significant resistance to microcatheter 8 advancement is encountered as evidenced by buckling of the microcatheter 8; or whichever of desired-alignment or significant resistance occurs first. While moving the deployed distal segment 13 toward or into the guide catheter, any of the following may occur: proximal guide lumen communicates with pressure bag or other positive pressure fluid source; proximal guide lumen communicates with atmosphere; or proximal guide lumen communicates with aspiration source or other negative pressure.

Thrombus removal methods of the present invention have unique advantages over known thrombus removal methods. When deployed accross a thrombus, the distal segment 1 creates intra-procedural flow 14 by creating a fluid path across the thrombus 12' (FIG. 4). In this way, the distal segment 13 significantly reduces the pressure drop across the thrombus 12', and accordingly significantly reduces the pressure related forces which would otherwise resist removal of the thrombus 12 (FIG. 5). Further, the fluid path is created by the deployed distal segment 13 separating a significant portion of the thrombus 12' circumference away from the vessel wall. In addition, expansion of volume-reduced form 6 creates an integrated mass where the mesh is embedded within the thrombus. As above, the distal portion of volume-reduced form 6 can produce a greater radial force (and may be in a hook-like configuration upon expansion) thereby facilitating removal of the thrombus.

It is estimated that about 10% to about 60% of the original thrombus 12 circumference is separated from the vessel wall after the distal segment 1 is deployed 13, and the ability of the post deployment thrombus 12' to hang onto the vessel wall via adhesion and friction is accordingly reduced. Still further, the cross sectional area of the original thrombus 12 is significantly reduced by the deployed distal segment 13, resulting in a thrombus 12' having about 30% to about 95% of its original cross sectional area, but more typically about 50% to about 80% of its original cross sectional area. All of this results in a more effective revascularization procedure as a result of lower thrombus dislodgement and mobilization force and more effective thrombus mobilzation 19, as demonstrated by the functions later described herein. Of further benefit, the lower thrombus mobilization force is distributed along the entire length of the thrombus 12', or at least along the entire length of the distal segment 13, reducing the chances of the apparatus slipping past or through the thrombus or fragmenting the thrombus, which could result in residual thrombus, distal embolization, or embolization of uninvolved territories.

A target occlusion is represented by an original thrombus 12 having cross sectional area A (FIG. 2a), creating an associated pressure drop across the thrombus of P, having circumferential vessel contact area C, and f is a quantity proportional to a ratio of the thrombus adhesive and frictional forces/contact area. The force required to dislodge or mobilize this thrombus by known methods that do not establish intra-procedural flow across the thrombus and do not separate a significant portion of the thrombus circumference away from the vessel wall can be described by the function:

$$(A*P)+C*f$$

For the thrombus removal methods of the present invention, that is when the distal segment 1 is deployed 13 within the thrombus 12' (FIG. 4), the thrombus 12' has reduced cross sectional area "a" where a<A, reduced pressure drop across the thrombus "p" where p<P, significantly reduced circumferential vessel contact area "c" where c<C, and f is a quantity proportional to a ratio of the thrombus adhesive and frictional forces/contact area. The force required to dislodge and mobilize the thrombus 12' according to the methods described herein will be significantly lower than forces required to dislodge and mobilized original thrombus 12 by known methods (FIG. 5), and can be described by the function:

$$(a*p)+c*f$$

Figure 6:
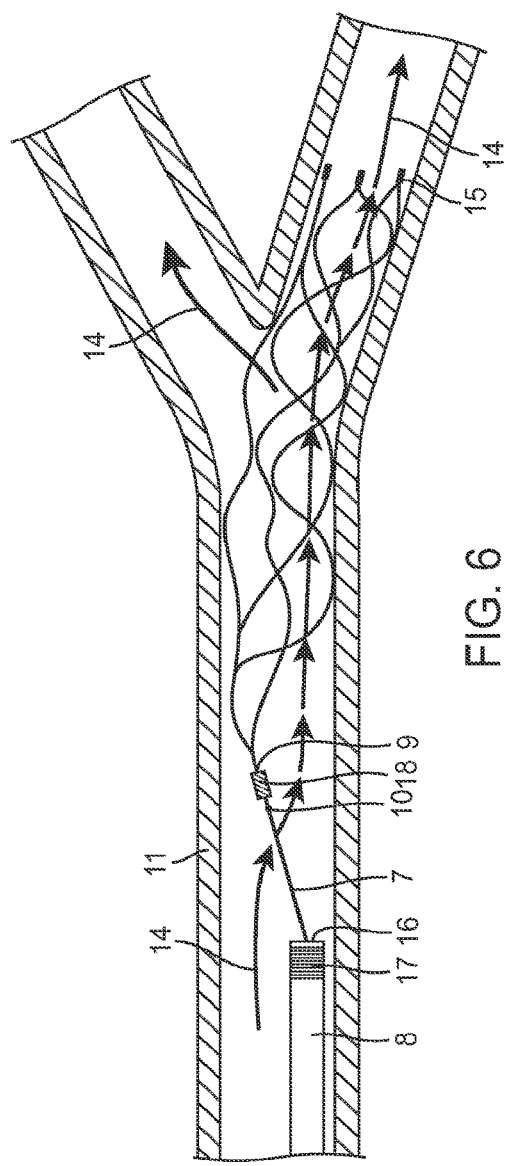
FIGS. 6 and 7 show thrombus dissolution methods according to the present invention.
Figure 7:
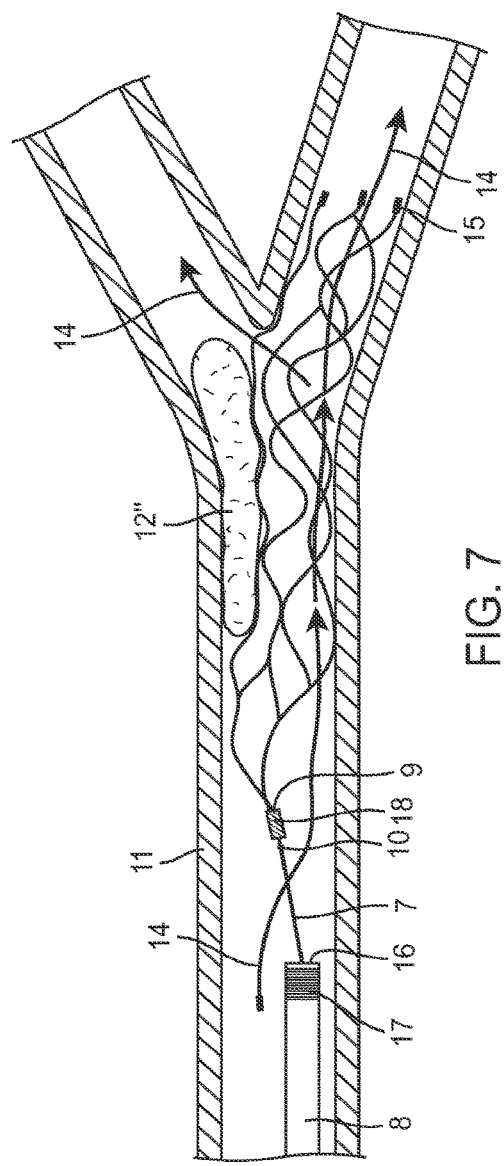
Figure 8:
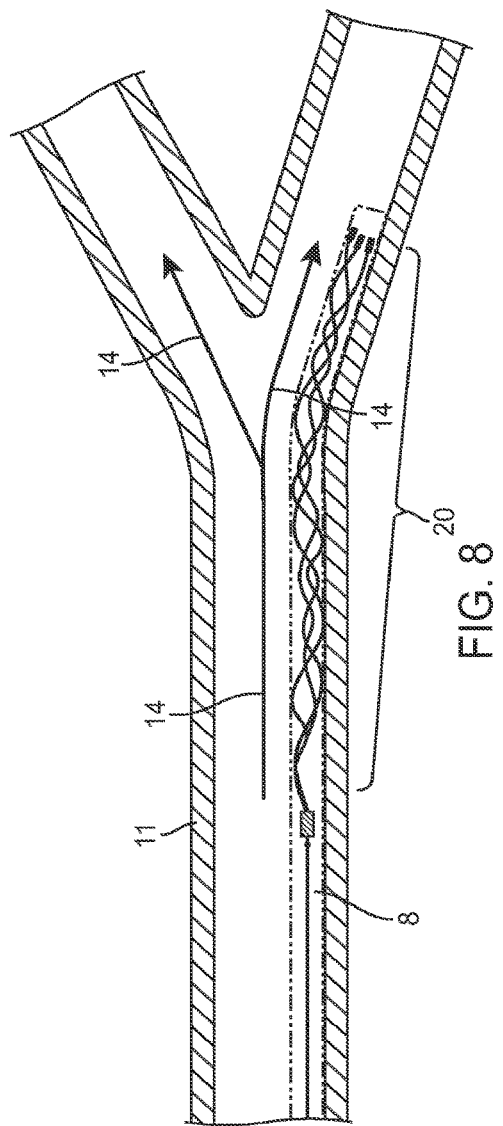
FIGS. 8 and 9 show apparatus retrieval methods according to the present invention, with the microcatheter shown in phantom.
Figure 9:
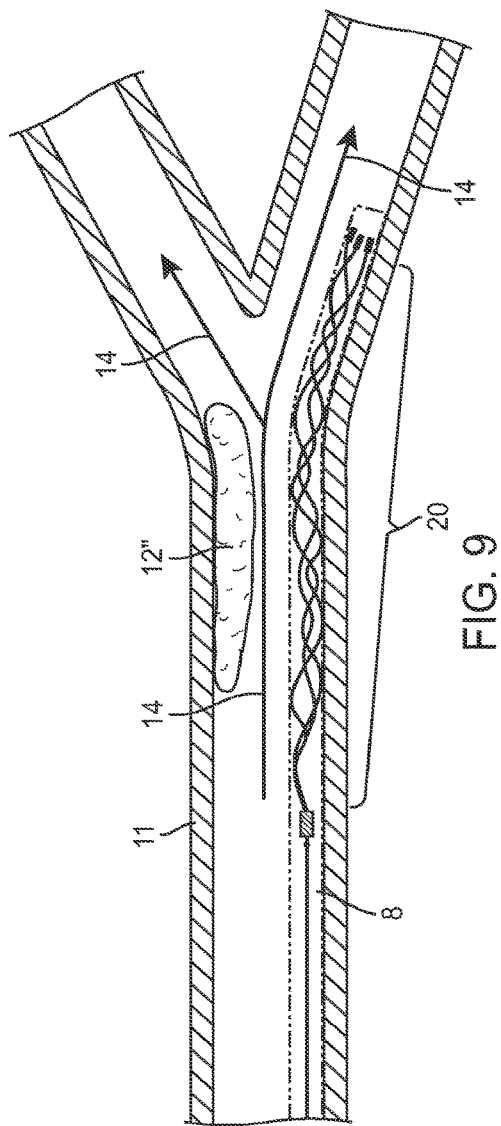

Also contemplated by the present invention are thrombus dissolution methods and apparatus that restore blood flow 14 in the occluded artery, with an increased efficiency in dissolving part (FIG. 7) or all (FIG. 6) of the thrombus from the vessel and retreival of the apparatus (FIGS. 8 and 9). As previously described, the distal segment is deployed within and across a thrombus 12' to restore blood flow 14 in the occluded artery (FIG. 4). Immediately reestablishing blood flow 14 is a significant advantage over know apparatus and methods for treating cerebral arteries occluded by thrombus because known apparatus and methods may take hours to reestablish flow. Specific benefits include reestablishing antegrade flow distal of the original occlusion to perfuse ischemic tissue and help break up emboli that may be present distal of the original occlusion. Additional benefit is derived from increasing the surface area of the thrombus 12' exposed to the blood flow, thereby improving the effectivity of natural lysing action of the blood on the thrombus 12' and improving the effectivity of the thrombolytic, anticoagulant, anti-platelet, or other pharmacological agents introduced by the physician, all of which facilitates thrombus dissolution. When the thrombus has been completely dissolved (FIG. 6), or sufficiently reduced 12" such that reocclusion is not likely (FIG. 7), the distal segment 1 is retrieved 20 by advancing the microcatheter 8 over the entire distal segment 1 while holding the push wire 7 in a fixed position such that the distal segment 1 is not moved axially within the artery (FIGS. 8 and 9). The apparatus may then be removed through the microcatheter 8 or alternatively the microcatheter 8 can be removed with the distal segment 1 of the apparatus still inside of it.

Additionally, it is contemplated that the methods of the present invention can restore blood flow in the occluded artery, with an increased efficiency in dissolving part or all of the thrombus from the vessel and implantation of the distal segment 1. Methods that include implantation of the distal segment 1 require the use of an apparatus with a releasable attachment mechanism between the distal segment 1 and push wire 7. As previously described, the distal segment 1 is deployed within and across 13 a thrombus 12' to restore blood flow 14 in the occluded artery (FIG. 4). The distal segment 1 can then be released from the push wire via a releasable attachment mechanism. Such release may occur immediately upon reestablishing blood flow (FIG. 10), when the thrombus 12" has been sufficiently reduced such that reocclusion is not likely (FIG. 11), or when the thrombus is completely dissolved (FIG. 12).

In another embodiment of the invention, the thrombus removal or dissolution is assisted by aspirating the microcatheter and/or the guide catheter.

Utility derived from a releasable mechanism between the distal segment and push wire includes suitability of one apparatus for all of the methods disclosed herein, providing procedural options for the user. Of futher benefit, a releasable mechanism enables the user to release the unconstrained distal segment if it is determined that removal from the patient is not possible.

Certain embodiments of the invention include methods of restoring blood flow and then detaching the apparatus and leaving the apparatus in situ (FIG. 12). This can be done when it is determined by the clinician that either the apparatus is no longer retrievable. In this embodiment, it is contemplated that the apparatus would be coated or otherwise embedded with anticoagulant or antiplatelet drugs. This is more thoroughly discussed below.

Apparatus

As mentioned above, any suitable self-expandable apparatus may be employed by the methods of the invention. Various embodiments of the apparatus may be found in U.S. Pat. No. 7,300,458, which is incorporated by reference in its entirety.

A distal segment 1, according to FIG. 13, consists of a mesh or honeycomb structure that, in one embodiment, comprises a multitude of filaments interconnected by a laser welding technique. The distal segment 1 can be subdivided into a functional structure A and a tapering proximal structure B, the two structures being distinguishable, inter alia, by a different mesh size. To enable the functional structure A to perform its function, its mesh cells 23 are held relatively narrow so that they lend themselves to the implantation into the thrombus 12. In general, the mesh width is in the range of 0.5 to 4 mm and may vary within the segment.

In one aspect of the present invention, the distal segment 1 is a flat or two-dimensional structure that is rolled up to form a longitudinally open object capable of establishing close contact with the wall of the vessel into which it is introduced.

In the tapering proximal structure B of the distal segment 1, there is provided a wider mesh cell 24 structure which has been optimized towards having a minimum expansion effect. In the area of the tapering structure 22, the filaments have a greater thickness and/or width to be able to better transfer to the functional structure A the thrust and tensile forces of the guide wire exerted at a connection point 9 when the distal segment 1 is introduced and placed in position. In the area of the tapering structure it is normally not necessary to provide support for, and coverage of, the vessel wall, but on the other hand requirements as to tensile and thrust strength increase. The filament thickness in the functional structure A generally ranges between 0.02 and 0.076 mm, and in proximal structure part B, the filament thickness is greater than 0.076 mm.

The proximal structure forms an angle from 45 degrees to 120 degrees at the connection point 9, in particular an angle of about 90 degrees. The filament thickness (or string width) is the same as the mesh size and its shape may vary over a great range to suit varying requirements as to stability, flexibility and the like. It is understood that the proximal structure B, as well, contacts the vessel wall and thus does not interfere with the flow of blood within the vessel.

At a distal end, the filaments 22 end in a series of tails 2 that are of suitable kind to carry platinum markers that facilitate the positioning of the distal segment 1.

The distal segment 1 is curled up in such a way that edges 27 and 28 are at least closely positioned to each other and may overlap in the area of the edges. In this volume-reduced form, the distal segment 1, similar to a wire mesh roll, has curled up to such an extent that the roll so formed can be introduced into a microcatheter and moved within the catheter. Having been released from the microcatheter, the curled-up structure springs open and attempts to assume the superimposed structure previously impressed on it and in doing so closely leans to the inner wall of the vessel to be treated, thus superficially covering a thrombus and then implanting into the thrombus that exists in that location. In this case the extent of the "curl up" is governed by the vessel volume. In narrower vessels a greater overlap of the edges 27 and 28 of the distal segment 1 will occur whereas in wider vessels the overlap will be smaller or even "underlap," will be encountered, and due care must be exercised to make sure the distal segment 1 still exhibits a residual tension.

Suitable materials that can be employed in the device include alloys having shape-memory properties. The finished product is subjected to a tempering treatment at temperatures customarily applied to the material so that the impressed structure is permanently established.

The distal segment 1 has a mesh-like structure consisting of strings or filaments connected with each other. Strings occur if the distal segment 1 comprises cut structures as, for example, are frequently put to use in coronary stents, a mesh-like structure consisting of filaments is found if the distal segment 1 is present in the form of mats having knitted or braided structures or in the form of individual filaments that are welded to one another.

FIG. 14 shows another embodiment of a distal segment 1 according to the invention having the above described honeycomb structure where the tapering proximal structure B is connected with the functional structure part A by additional filaments 29 in a peripheral area 30 as well as in the central area. The additional filaments 29 and 30 bring about a more uniform transmission of the tensile and thrust forces from the proximal structure B to the functional structure A. As a result, the tensile forces can be better transmitted, especially if the stent might have to be repositioned by having to be retracted into the microcatheter. The additional filaments 29, 30 facilitate the renewed curling up of the stent. Similarly, the transmission of thrust forces occurring when the stent is moved out and placed in position is facilitated so that the stent can be gently applied.

FIG. 15 shows another embodiment of a distal segment 1 according to the invention having a honeycomb structure with the edges 27 and 28 being formed of straight filaments 29. According to this embodiment, the thrust or pressure exerted by the guide wire at the connection point 9 is directly transmitted to the edges 27 and 28 of the functional structure part A which further increases the effect described with reference to FIG. 14.

The embodiment as per FIG. 15, similar to those depicted in FIGS. 13 and 14, may be based on a cut foil, i.e., the individual filaments 22, 29 and 30 are substituted by individual strings being the remaining elements of a foil processed with the help of a cutting technique. Laser cutting techniques for the production of stents having a tubular structure are known. The processing of a foil for the production of a pattern suitable for a stent is performed analogously. The impression of the superimposed structure is carried out in the same way as is used for the filament design.

In one embodiment, expanded metal foil may be used with the respective string widths being of the same magnitude. In one embodiment, it is envisioned to subsequently smooth the foil to make sure all strings are arranged on the same plane. The thickness of the foil usually ranges between 0.02 and 0.2 mm. Foils of greater thickness also permit the stent to be used in other fields of application, for example, as coronary stents or in other regions of the body including, for instance, the bile duct or ureter.

Foils worked with the help of a cutting technique are finished by electrochemical means to eliminate burrs and other irregularities to achieve a smooth surface and round edges. One of ordinary skill in the art will understand these electrochemical processes as these processes already are in use in medical technology. In this context, it is to be noted that the stents according to the invention that are based on a two-dimensional geometry and on which a three-dimensional structure is impressed subsequently can be manufactured and processed more easily than the conventional "tubular" stents that already, during manufacture, have a three-dimensional structure and necessitate sophisticated and costly working processes and equipment.

As pointed out above, the mesh structure of the distal segment 1 according to the invention may consist of a braiding of individual filaments. Such a knitted structure is shown in FIG. 16 where the individual filaments 22 are interwoven in the form of a "single jersey fabric" having individual loops 23 forming a mesh-like structure 31. Single jersey goods of this type are produced in a known manner from a row of needles. The single jersey goods have two fabric sides of different appearance, i.e., the right and left side of the stitches. A single jersey fabric material features minor flexibility in a transverse direction and is very light.

Filaments consisting of a braid of individual strands and formed into a rope can also be employed. Braids comprising twelve to fourteen strands having a total thickness of 0.02 mm can be used. Platinum, platinum alloys, gold and stainless steel can be used as materials for the filaments. Generally speaking, all permanent distal segment 1 materials known in medical technology can be employed that satisfy the relevant requirements.

In one embodiment, it is advantageous to have the fabric rims of such a knitted structure curling up as is known, for example, from the so-called "Fluse" fabric, a German term, which is of benefit with respect to the superimposed structure and application dealt with here. In this case, the superimposed structure can be impressed by means of the knitting process. However, the use of shape-memory alloys in this case as well is feasible and useful.

For the production of such knitted structures, known knitting processes and techniques can be employed. However, since the distal segments according to the invention are of extremely small size—for example, a size of 2 by 1 cm—it has turned out to be beneficial to produce the distal segments in the framework of a conventional warp or weft knitting fabric of textile, non-metallic filaments, for example, in the form of a rim consisting of the respective metallic filaments from which the weft or warp knitting fabric either starts out or that extends from such a fabric. The arrangement of the metallic part of the weft or warp knitting fabric at the rim achieves the aforementioned curling effect. The non-metallic portions of the knitted fabric are finally removed by incineration, chemical destruction or dissolution using suitable solvents.

FIG. 1 shows a combination of a guide wire 7 with the distal segment 1 attached to it that consists of filaments connected to each other by welding. The distal ends 2 and the connection point 9 where the filaments of the distal segment 1 converge in a tapering structure and that simultaneously represents the joining location with guide wire 7 are shown. The guide wire 7 is introduced into a microcatheter 8 which is of customary make.

Shifting the guide wire 7 within the catheter 8 will cause the distal segment 1 to be pushed out of or drawn into the catheter. Upon the stent being pushed out of the microcatheter 8 the mesh-like structure attempts to assume the superimposed shape impressed on it, and when being drawn in, the mesh structure folds back into the microcatheter 8 adapting to the space available inside.

As a result of the stiffness of its mesh structure, the distal segment 1 can be moved to and fro virtually without restriction via the guide wire 7 until it has been optimally positioned within the vessel system.

As mentioned earlier, customary microcatheters can be used. One advantage of the distal segment 1 according to the invention and of the combination of distal segment 1 and guide wire according to the invention is, however, that after having placed the microcatheter in position with a customary guide wire/marker system, the combination of guide wire 7 and distal segment 1 according to the invention can be introduced into the microcatheter, moved through it towards the implantation site and then moved out and applied in that position. Alternatively, it will be possible to have a second microcatheter of smaller caliber accommodate guide wire 7 and distal segment 1 and with this second microcatheter within the firstly positioned microcatheter shift them to the implantation site. In any case, the distal segment 1 can be easily guided in both directions.

FIG. 17 shows a schematic representation of an distal segment 1 according to the invention in its superimposed or volume-expanded shape and in its volume-reduced shape. In its expanded shape, as illustrated in FIG. 17*a*, the distal segment 1 forms a ring-shaped structure with slightly overlapping edges 27 and 28. In FIG. 17*a* the distal segment 1 is viewed from its proximal end as a top view with the connection point 9 being approximately positioned opposite to the edges 27 and 28. In the combination according to the invention, the guide wire 7 is affixed at the connection point 9.

FIG. 17*b* shows the same distal segment 1 in its volume-reduced form 6 as it is arranged, for example, in a microcatheter in a curled up condition. In the case illustrated there is a total of two windings of the curled-up distal segment 1 with the connection point 9 being located at the proximal side and the two lateral edges 27 and 28 being the starting and final points of the roll or spiral. The structure is held in its volume-reduced form by the microcatheter 8 and when the distal segment 1 is pushed out of the microcatheter 8 it springs into its expanded shape, as illustrated by FIG. 17*a*, similar to a spiral spring.

Figure 18A:
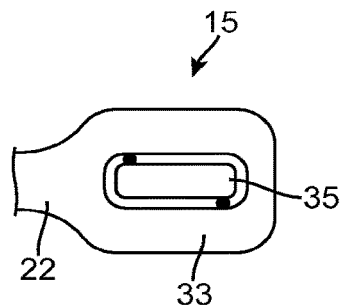
FIG. 18a, FIG. 18b, FIG. 18c, FIG. 18d, and FIG. 18e are embodiments, including marker elements, that can be employed in the most distal segment of the apparatus according to the present invention.
Figure 18B:
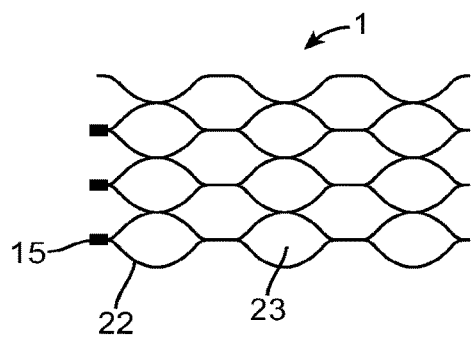

FIG. 18*a* shows a marker element 15 suitable for the distal segment 1 according to the invention with the marker element 15 being capable of being arranged at the distal end of the distal segment 1. The marker element 15 consists of a lug 33 provided with a small marker plate 35 levelly arranged inside it, i.e., flush with the plane of the distal segment 1 without any projecting elements. The plate 35 is made of an X-ray reflecting material, for example, platinum or platinum-iridium. The marker plate 35 may be connected to the surrounding distal segment 1 structure by known laser welding techniques. As shown in FIG. 18*b*, the marker elements 15 are arranged at the distal end of the distal segment 1.

Figure 18C:
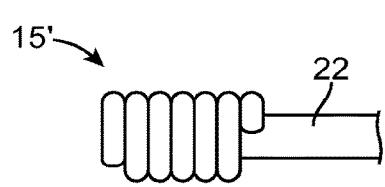
Figure 18D:
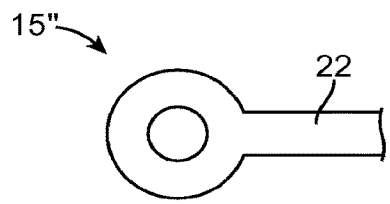
Figure 18E:
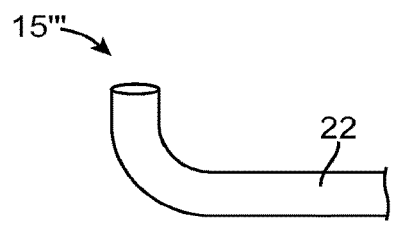

As mentioned above, in one embodiment, the apparatus is configured to so as to provided a removable, integrated thrombus apparatus-mass. This configuration can be done in a variety of ways. For example, as can be seen in FIG. 18*c*, marker element 15' can be provided in a spiral thereby increasing the support of the distal end of the mesh structure and aiding in the thrombus retrieval. Also, as seen in FIG. 18*d*, the marker element 15' can be provided as an eyelet shape functioning in a manner similar to the spiral marker 15'. FIG. 18*e* shows a marker element 15" shown in the shape of a hook or a peg which can be added to provide additional retention of the thrombus during removal. Marker element 15' is optionally radiopaque or may be made from the same shape memory alloy as the mesh structure.

Additional structural configurations contemplated to provide a removal, integrated thrombus apparatus-mass include: 1) a greater diameter of the mesh structure in the most distal location of the distal segment 1 compared to the proximal end of the mesh structure (or a widening-taper on the distal end of the distal segment 1); 2) a third plurality of mesh cells located in the most distally in the distal segment 1, wherein the this third plurality of mesh cells have smaller mesh size compared to the first plurality of mesh cells; 3) adding synthetic polymers or polymeric fibers to the mesh structure; and 4) heating the distal end of the distal segment 1 for a time sufficient to impart increased radial strength for better thrombus retention.

As mentioned above, fibers may be added to the mesh structure. Fibers may be wrapped or wound around the mesh structure. They may have loose ends or may be fully braided throughout the distal segment 1.

Suitable fibers are taught in US Publication 2006/0036281, which is incorporated by reference in its entirety. In certain embodiments, the fibers may be comprised of polymeric materials. The polymeric materials may include materials approved for use as implants in the body or which could be so approved. They may be nonbiodegradable polymers such as polyethylene, polyacrylics, polypropylene, polyvinylchloride, polyamides such as nylon, e.g., Nylon 6.6, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. In certain specific embodiments the nonbiodegradable materials for the polymer component may comprise polyesters, polyethers, polyamides and polyfluorocarbons.

The polymers can be biodegradable as well. Representative biodegradable polymers include: polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polylactic acid (PLA), polyglycolic acid (PGA), poly (p-dioxanone), poly (valetolactone), poly (tartronic acid), poly (β malonic acid), poly (propylene fumarate), poly (anhydrides); and tyrosine-based polycarbonates. Additional polymers contemplated include polyglycolide and poly-L-lactide.

Other equivalent materials, including but not limited to stereoisomers of any of the aforementioned, may be used as well.

Figure 19A:
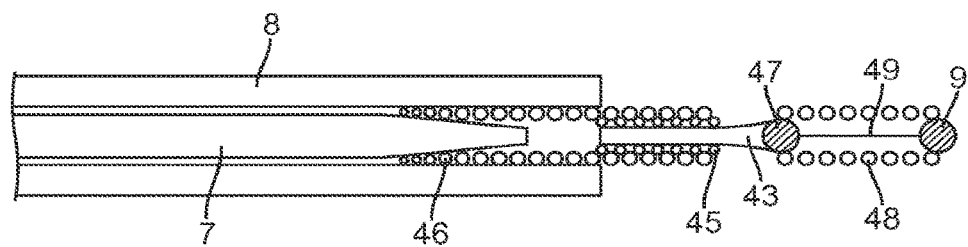
FIG. 19a and FIG. 19b are schematic representations of two detachment locations by which the apparatus, according to the present invention, can be detachably linked to a guide wire.
Figure 19B:
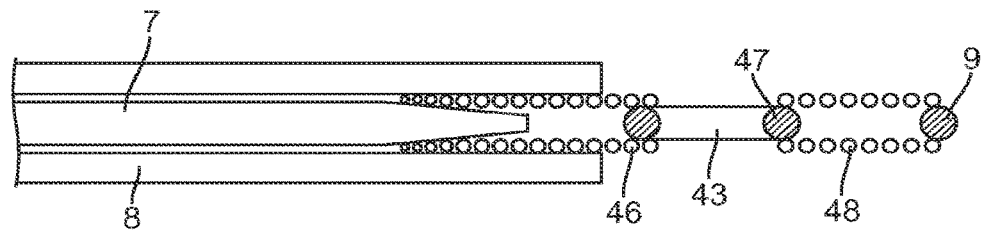

FIGS. 19a and 19b are representations, respectively, of two variations of a separating arrangement by which the distal segment 1 according to the invention is detachably connected to a guide wire 7. In each case, a separating arrangement consists of a dumb-bell shaped element 43 that dissolves under the influence of electrical energy when in contact with an electrolyte. At the proximal (guidewire side) end of the dumb-bell shaped separating element 43, as per FIG. 19a, a spiral structure 45 is located that interacts with a strengthening spiral 46 of the guide wire 7. At the distal end, a ball-shaped element 47 is arranged that, with the help of a laser welding technique, is connected to a platinum spiral 48 which, in turn, is linked with the connection point 9 situated at the proximal end of the distal segment 1. The platinum spiral 48 also serves as an X-ray reflecting proximal marker of the distal segment 1.

To strengthen the joint between the ball-shaped element 47 and the connection point 9, a reinforcement wire 49 may be provided. Alternatively, the platinum spiral 48 may also be designed in such a manner that it withstands the tensile and thrust forces imposed on it.

The separating element 43 can include a steel material that is susceptible to corrosion in an electrolyte under the influence of electrical energy. To accelerate corrosion and shorten the separating time span, a structural or chemical weakening of the dumb-bell shaped element 43 may be beneficial, for example, by applying grinding methods or thermal treatment.

Generally, the portion of the dumb-bell 43 accessible to the electrolyte has a length of 0.1 to 0.5 mm, particularly 0.3 mm.

The spiral structure 45 is secured via welding both to the dumb-bell shaped element 43 and the reinforcement spiral 46 of the guide wire 7. The guide wire 7 itself is slidably accommodated within the microcatheter 8.

FIG. 19b shows a second embodiment that differs from the one described with respect to FIG. 19a, in that the dumb-bell shaped element 43 has a ball-shaped element 47 at each end. The ball shaped elements 47 are connected distally to the connection point 9 of the distal segment 1 and proximally to the guide wire 7 via spirals 48, 46, respectively.

It is of course also provided that other separating principles may be applied, for example, those that are based on mechanical principles or melting off plastic connecting elements.

Coated Apparatus

This invention also contemplates coating the apparatus with anticoagulant and/or an antiplatelet agent or drug. It is contemplated that a drug may be used alone or in combination with another drug.

Anticoagulant agents or anticoagulants are agents that prevent blood clot formation. Examples of anticoagulant agents include, but are not limited to, specific inhibitors of thrombin, factor IXa, factor Xa, factor XI, factor XIa, factor XIIa or factor VIIa, heparin and derivatives, vitamin K antagonists, and anti-tissue factor antibodies, as well as inhibitors of P-selectin and PSGL-1. Examples of specific inhibitors of thrombin include hirudin, bivalirudin (Angiomax®), argatroban, ximelagatran (Exanta®,), dabigatran, and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Organ®); and synthetic pentasaccharide, such as fondaparinux (Arixtra®), idraparinux and biotinylated idraparinux. Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol.

Antiplatelet agents or platelet inhibitors are agents that block the formation of blood clots by preventing the aggregation of platelets. There are several classes of antiplatelet agents based on their activities, including, GP IIb/IIIa antagonists, such as abciximab (ReoPro®), eptifibatide (Integrilin®), and tirofiban (Aggrastat®); P2Y12 receptor antagonists, such as clopidogrel (Plavix®), ticlopidine (Ticlid®), cangrelor, ticagrelor, and prasugrel; phosphodiesterase III (PDE III) inhibitors, such as cilostazol (Pletal®), dipyridamole (Persantine®) and Aggrenox® (aspirin/extended-release dipyridamole); thromboxane synthase inhibitors, such as furegrelate, ozagrel, ridogrel and isbogrel; thromboxane A2 receptor antagonists (TP antagonist), such as ifetroban, ramatroban, terbogrel, (3-{6-[(4-chlorophenylsulfonyl)amino]-2-methyl-5,6,7,8-tetrahydronaphth-1-yl}propionic acid (also known as Servier S 18886, by de Recherches Internationales Servier, Courbevoie, France); thrombin receptor antagonists, such as SCH530348 (having the chemical name of ethyl (1R,3aR,4aR,6R, 8aR, 9S, 9aS)-9-((E)-2-(5-(3 fluorophenyl)pyridin-2-yl)vinyl)-1-methyl-3-oxododecahydronaphtho[2,3-C] furan-6-ylcarbamate, by Schering Plough Corp., New Jersey, USA, described in US2004/0192753A1 and US2004/0176418A1 and studied in clinical trials, such as A Multicenter, Randomized, Double-Blind, Placebo-Controlled Study to Evaluate the Safety of SCH 530348 in Subjects Undergoing Non-Emergent Percutaneous Coronary Intervention with ClinicalTrials.gov Identifier: NCT00132912); P-selectin inhibitors, such as 2-(4-chlorobenzyl)-3-hydroxy-7,8,9,10-tetrahydrobenzo[H]quinoline-4-carboxylic acid (also known as PSI-697, by Wyeth, New Jersey, USA); and non-steroidal anti-inflammatory drugs (NSAIDS), such as acetylsalicylic acid (Aspirin®), resveratrol, ibuprofen (Advil®, Motrin®), naproxen (Aleve®, Naprosyn®), sulindac (Clinoril®), indomethacin (Indocin®), mefenamate, droxicam, diclofenac (Cataflam®, Voltaren®), sulfinpyrazone (Anturane®), and piroxicam (Feldene®). Among the NSAIDS, acetylsalicylic acid (ASA), resveratrol and piroxicam are preferred. Some NSAIDS inhibit both cyclooxygenase-1 (cox-1) and cyclooxygenase-2 (cox-2), such as aspirin and ibuprofen. Some selectively inhibit cox-1, such as resveratrol, which is a reversible cox-1 inhibitor that only weakly inhibits cox-2.

In one embodiment, a controlled delivery of the drug can control the lytic effect of the drug and treat ischemic stroke and many other vascular diseases. The release rate can be controlled such that about 50% of the drug can be delivered to the thrombus in from about 1 to about 120 minutes. This controlled delivery can be accomplished in one or more of the following ways. First, the drug and polymer mixture may be applied to the stent and the amount of polymer may be increased or the combination may be applied in a thicker layer. Second, the stent may be first coated with polymer, then coated with a layer of drug and polymer, and then a topcoat of polymer can be applied. The release rates of the drug can be altered by adjusting the thickness of each of the layers. Third, the stent can be manufactured to provide reservoirs to hold the drug. In this embodiment, the drug is filled in small reservoirs made on the stent surface. Reservoirs can be made by laser cutting, machine electro-chemical, mechanical or chemical processing.

In the embodiments just described the polymer is biocompatible and biodegradable. These polymers are well known in the art.

Additionally, stents can be coated with a drug-eluting coating such as a combination of a polymer and a pharmaceutical agent. Such coatings can be applied using methods well established in the art, such as dipping, spraying, painting, and brushing. See, U.S. Pat. Nos. 6,214,115; 6,153,252; U.S. patent application No. 2002/0082679; U.S. Pat. Nos. 6,306,166; 6,517,889; 6,358,556; 7,318,945; 7,438,925.

For example, Chudzik et al. (U.S. Pat. No. 6,344,035) teaches a method wherein a pharmaceutical agent or drug is applied in combination with a mixture of polymers such as poly(butyl methacrylate) and poly(ethylene-co-vinyl acetate). Guruwaiya et al. discloses a method for coating a stent wherein a pharmacological agent is applied to a stent in dry, micronized form over a sticky base coating (U.S. Pat. No. 6,251,136). Ding et al. teaches a method of applying drug-release polymer coatings that uses solvents (U.S. Pat. No. 5,980,972) wherein the solutions are applied either sequentially or simultaneously onto the devices by spraying or dipping to form a substantially homogenous composite layer of the polymer and the pharmaceutical agent.

Although various exemplary embodiments of the present invention have been disclosed, it will be apparent to those skilled in the art that changes and modifications can be made which will achieve some of the advantages of the invention without departing from the spirit and scope of the invention. It will be apparent to those reasonably skilled in the art that other components performing the same functions may be suitably substituted.

What is claimed is:

1. A removable, integrated apparatus-thrombus mass, comprising a thrombus at least partially engaged with an apparatus, wherein the apparatus comprises:
    a self-expandable structure comprising a first plurality of cells, the structure having a proximal end and a distal end, the proximal end and the distal end being open, and the first plurality of cells being expanded into at least a portion of the thrombus;
    a tapering portion comprising a second plurality of cells, the tapering portion disposed toward the proximal end of the structure;
    a connection portion, at which the tapering portion converges, located at a proximal end of the tapering portion; and
    a push or guide wire, wherein a distal end of the push or guide wire is non-releasably attached at or adjacent to the connection portion,
    wherein the apparatus is self-expandable and pre-formed to assume a volume-enlarged form and, in the volume-enlarged form, takes the form of a longitudinally open tube tapering toward the connection portion.

2. The removable, integrated apparatus-thrombus mass of claim 1, wherein a mesh size of the second plurality of cells is larger than a mesh size of the first plurality of cells.

3. The removable, integrated apparatus-thrombus mass of claim 2, wherein the structure has a distal portion comprising a third plurality of cells distal to the first plurality of cells, the third plurality of cells having a mesh size smaller than the mesh size of the first plurality of cells.

4. The removable, integrated apparatus-thrombus mass of claim 1, wherein the distal end of the structure is heated for a sufficient time to provide increased radial strength.

5. The removable, integrated apparatus-thrombus mass of claim 1, wherein the distal end of the structure comprises fibers.

6. The removable, integrated apparatus-thrombus mass of claim 1, wherein the distal end of the structure comprises one or more pegs and/or hooks.

7. The removable, integrated apparatus-thrombus mass of claim 1, wherein the structure is coated with an anticoagulant or antiplatelet drug.

8. The removable, integrated apparatus-thrombus mass of claim 7, wherein the structure is further coated with a biodegradable, biocompatible polymer to provide for sustained release of the anticoagulant or antiplatelet drug.

9. The removable, integrated apparatus-thrombus mass of claim 1, wherein the structure comprises reservoirs to hold an anticoagulant or antiplatelet drug.

10. The removable, integrated apparatus-thrombus mass of claim 1, wherein the apparatus can take a volume-reduced form, and the structure forms edges and is curled up such that the edges overlap in the volume-reduced form, and wherein in the volume-enlarged form the edges overlap less than in the volume-reduced form.

11. The removable, integrated apparatus-thrombus mass of claim 1, further comprising radiopaque markers on the distal end of the structure.

12. The removable, integrated apparatus-thrombus mass of claim 11, wherein the radiopaque markers are attached to distal tails at the distal end of the structure.

13. The removable, integrated apparatus-thrombus mass of claim 1, further comprising a radiopaque marker at a proximal end of the tapering portion.

14. The removable, integrated apparatus-thrombus mass of claim 1, further comprising fibers wrapped or wound around the structure.

15. The removable, integrated apparatus-thrombus mass of claim 1, wherein the integrated apparatus-thrombus mass is removable by retracting the push or guidewire through a blood vessel.

16. The removable, integrated apparatus-thrombus mass of claim 1, wherein the first plurality of cells are embedded within the thrombus.

17. The removable, integrated apparatus-thrombus mass of claim 1, wherein the first plurality of cells are implanted into the thrombus.

18. A removable, integrated apparatus-thrombus mass, comprising a thrombus at least partially engaged with a self-expandable apparatus, wherein the apparatus comprises:
- a self-expandable structure comprising a first plurality of cells, the structure having a proximal end and a distal end, the proximal end and the distal end being open, and the first plurality of cells being expanded into and interlocked with at least a portion of the thrombus;
- a tapering portion comprising a second plurality of cells, the tapering portion disposed toward the proximal end of the structure; and
- a connection member, toward which the tapering portion converges, located at a proximal end of the tapering portion; and
- a push or guide wire, and wherein a distal end of the push or guide wire is non-releasably attached to the tapering portion at or adjacent to the connection member,
- wherein the self-expandable apparatus is configured to assume a volume-enlarged form and, in the volume-enlarged form, to take the form of a longitudinally open tube; and
- wherein the thrombus extends outside of the structure.

19. The removable, integrated apparatus-thrombus mass of claim 18, wherein a mesh size of the second plurality of cells is larger than a mesh size of the first plurality of cells.

20. The removable, integrated apparatus-thrombus mass of claim 19, wherein the structure has a distal portion comprising a third plurality of cells distal to the first plurality of cells, the third plurality of cells having a mesh size smaller than the mesh size of the first plurality of cells.

21. The removable, integrated apparatus-thrombus mass of claim 18, wherein the distal end of the structure is heated for a sufficient time to provide increased radial strength.

22. The removable, integrated apparatus-thrombus mass of claim 18, wherein the distal end of the structure comprises fibers.

23. The removable, integrated apparatus-thrombus mass of claim 18, wherein the distal end of the structure comprises one or more pegs and/or hooks.

24. The removable, integrated apparatus-thrombus mass of claim 18, wherein the structure is coated with an anticoagulant or antiplatelet drug.

25. The removable, integrated apparatus-thrombus mass of claim 24, wherein the structure is further coated with a biodegradable, biocompatible polymer to provide for sustained release of the anticoagulant or antiplatelet drug.

26. The removable, integrated apparatus-thrombus mass of claim 18, wherein the structure comprises reservoirs to hold an anticoagulant or antiplatelet drug.

27. The removable, integrated apparatus-thrombus mass of claim 18, wherein the apparatus can take a volume-reduced form, and the structure forms edges and is curled up such that the edges overlap in the volume-reduced form, and wherein in the volume-enlarged form the edges overlap less than in the volume-reduced form.

28. The removable, integrated apparatus-thrombus mass of claim 18, further comprising radiopaque markers on the distal end of the structure.

29. The removable, integrated apparatus-thrombus mass of claim 28, wherein the radiopaque markers are attached to distal tails at the distal end of the structure.

30. The removable, integrated apparatus-thrombus mass of claim 18, further comprising a radiopaque marker at a proximal end of tapering portion.

31. The removable, integrated apparatus-thrombus mass of claim 18, further comprising fibers wrapped or wound around the structure.

32. The removable, integrated apparatus-thrombus mass of claim 18, wherein the integrated apparatus-thrombus mass is removable by retracting the push or guidewire through a blood vessel.

33. The removable, integrated apparatus-thrombus mass of claim 18, wherein the first plurality of cells are embedded within the thrombus.

34. The removable, integrated apparatus-thrombus mass of claim 18, wherein the first plurality of cells are implanted into the thrombus.

* * * * *

UNITED STATES PATENT AND TRADEMARK OFFICE
CERTIFICATE OF CORRECTION

PATENT NO. : 10,456,151 B2  
APPLICATION NO. : 14/885826  
DATED : October 29, 2019  
INVENTOR(S) : Slee et al.

It is certified that error appears in the above-identified patent and that said Letters Patent is hereby corrected as shown below:

On the Title Page

Item "(72)", Column 1, in "Inventors", Line 2, delete "Wilder," and insert -- Wilder III, --, therefor.

Signed and Sealed this  
Twenty-fifth Day of February, 2020

Andrei Iancu  
*Director of the United States Patent and Trademark Office*